United States Patent [19]

Flammang

[11] Patent Number: 5,782,876

[45] Date of Patent: Jul. 21, 1998

[54] METHOD AND APPARATUS USING WINDOWS AND AN INDEX VALUE FOR IDENTIFYING CARDIC ARRHYTHMIAS

[75] Inventor: Daniel Flammang, Angouleme, France

[73] Assignee: Medtronic, Inc., Minneapolis, Minn.

[21] Appl. No.: 632,699

[22] Filed: Apr. 15, 1996

[51] Int. Cl.$^6$ .............................. A61N 1/362; A61N 1/368
[52] U.S. Cl. .................................................................. 607/4
[58] Field of Search .............................................. 607/4, 5

[56] References Cited

U.S. PATENT DOCUMENTS

| | | |
|---|---|---|
| 4,310,000 | 1/1982 | Lindemans . |
| 4,505,276 | 3/1985 | Markowitz . |
| 4,523,595 | 6/1985 | Zibell . |
| 4,543,963 | 10/1985 | Gessman . |
| 4,585,004 | 4/1986 | Browniee . |
| 4,686,988 | 8/1987 | Sholder . |
| 4,712,554 | 12/1987 | Garson, Jr. . |
| 4,754,753 | 7/1988 | King . |
| 4,759,366 | 7/1988 | Callaghan . |
| 4,817,605 | 4/1989 | Sholder . |
| 4,825,869 | 5/1989 | Sasmor et al. . |
| 4,873,980 | 10/1989 | Schaldach . |
| 4,917,115 | 4/1990 | Flammang . |
| 4,960,123 | 10/1990 | Maker . |
| 5,063,928 | 11/1991 | Grevis et al. ............... 607/4 |
| 5,172,694 | 12/1992 | Flammang et al. . |
| 5,181,519 | 1/1993 | Bible . |
| 5,193,535 | 3/1993 | Bardy et al. ............... 607/4 |
| 5,257,621 | 11/1993 | Bardy et al. ............... 607/4 |
| 5,312,441 | 5/1994 | Mader et al. . |
| 5,312,445 | 5/1994 | Nappholz et al. . |
| 5,330,513 | 7/1994 | Nichols et al. ............ 607/32 |
| 5,331,966 | 7/1994 | Bennett et al. . |
| 5,355,891 | 10/1994 | Wateridge et al. . |
| 5,381,803 | 1/1995 | Herleikson et al. . |
| 5,447,519 | 9/1995 | Peterson ....................... 607/4 |
| 5,645,574 | 7/1997 | Bouhour et al. ............. 607/17 |

FOREIGN PATENT DOCUMENTS

| | | | |
|---|---|---|---|
| 0623364 | 11/1994 | European Pat. Off. ......... | A61N 1/39 |
| 9004942 | 5/1990 | WIPO ........................... | A61B 5/0432 |

OTHER PUBLICATIONS

"Discrimination of antegrade and retrograde atrial depolarization by electrogram analysis" by Pannizzo et al, Dpt. Surgery Div. Cardiothoracic Surg., 1985 p. 780.
Abstract: "Tiered intraatrial electrograms bases for a rhythmological diagnosis system", by Flammang et al, #576 from Cardiostim 92., Eur.J.C.P.E., vol. 2, Jun. 1992.

*Primary Examiner*—William E. Kamm
*Assistant Examiner*—Carl H. Layno
*Attorney, Agent, or Firm*—Michael J. Jaro; Harold Patton

[57] ABSTRACT

A method and apparatus for identifying cardiac arrhythmias. In the preferred embodiment the invention is embodied in an implantable pulse generator. The IPG features a system to analyze the sensed ECG. The system utilizes an algorithm able to quantify continuously the sensed cardiac rhythm. The algorithm features essentially two parts, a pre-diagnostic program ("PDP"), which is able to discriminate up to 95% of all sensed rhythms, and a diagnostic program ("DP"), which is able to discriminate the remaining sensed rhythms. The pre-diagnostic program is relatively quicker and draws less energy as compared to the diagnostic program. The pre-diagnostic program functions by regularly measuring the dv/dt of the sensed ECG. These values are then converted into an index value to thereby quantify the sensed cardiac rhythm. After any noise is rejected, the algorithm permits an automatic discrimination of normal sinus rhythm from atrial fibrillation, atrial flutter, ventricular tachycardia, ventricular fibrillation and ventricular flutter. In cases where other rhythms are sensed, the algorithm then utilizes the diagnostic program. The diagnostic program compares a series of sensed values from the sensed ECG to a series of references values. Through the various values examined, a discrimination among various arrhythmias is accomplished.

19 Claims, 15 Drawing Sheets

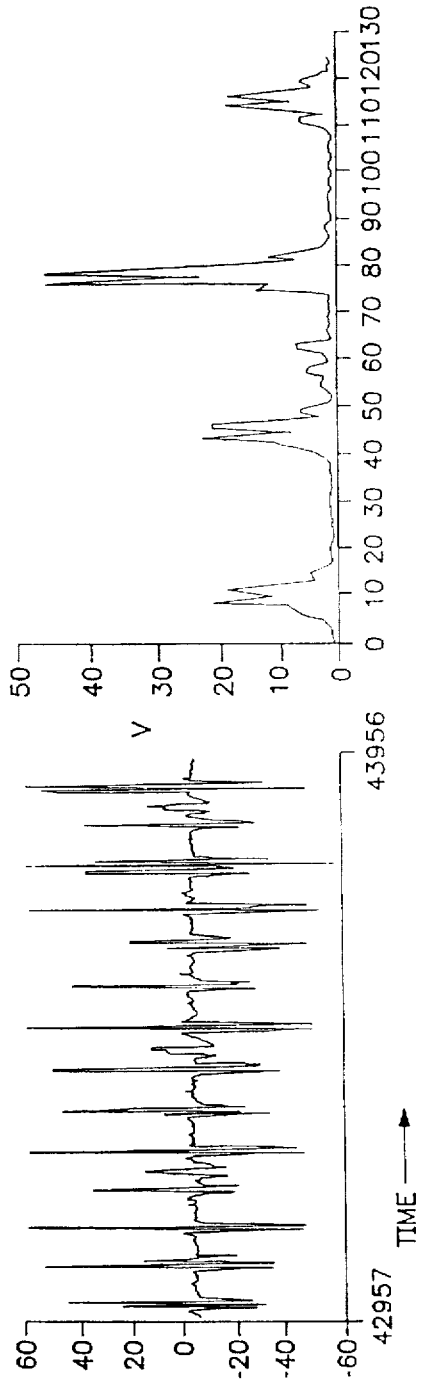
FIG. 8A
FIG. 8B
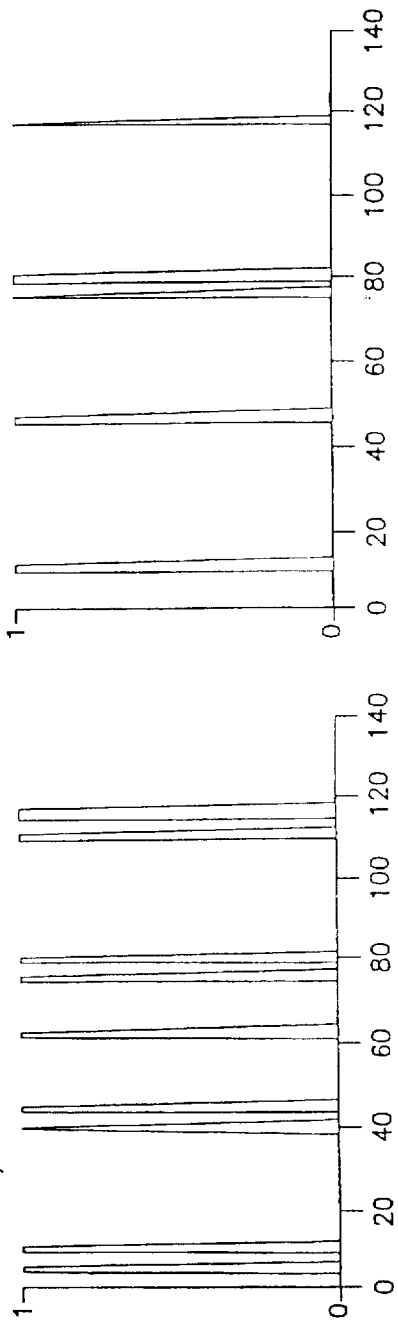
FIG. 8C
FIG. 8D

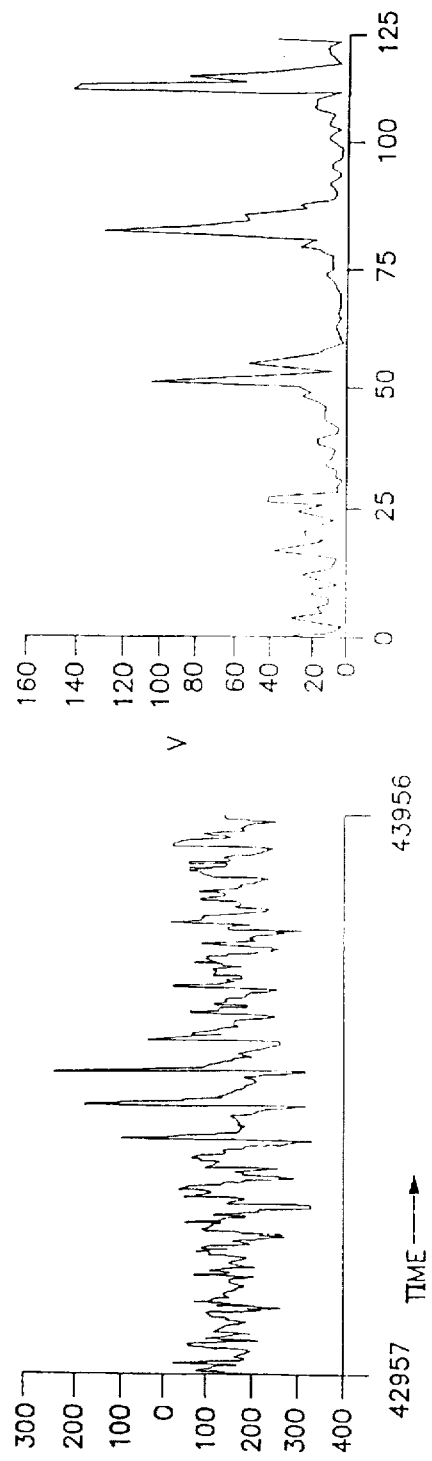
FIG. 9A
FIG. 9B
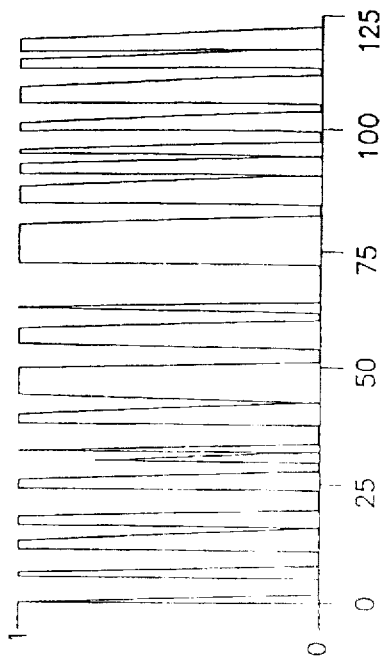
FIG. 9C
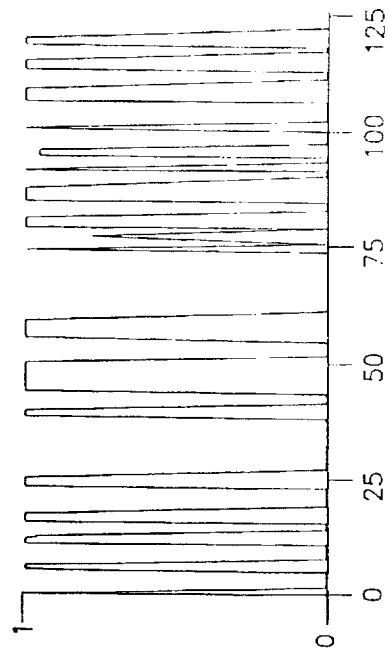
FIG. 9D

| IF DV/DT INDEX EQUALS: | THEN THE DIAGNOSIS OF THE PDP IS: |
|---|---|
| HIGH RIGHT ATRIAL ELECTRODE | |
| 0-3 | NORMAL SINUS RHYTHM |
| 3-6 | ATRIAL FLUTTER |
| 6-12 | ATRIAL FIBBRILLATION |
| 3-8 | ATRIAL FIBRILLO-FLUTTER |
| VENTRICULAR ELECTRODE | |
| 0-2 | NORMAL SINUS RHYTHM |
| 2-4 | VENTRICULAR TACHYCARDIA (LESS THAN 220 BPM) |
| 4-6 | VENTRICULAR FLUTTER (250-350 BPM) |
| 6-9 | VENTRICULAR FIBRILLATION (350+BPM) |

FIG. 10

| DIAGNOSES | DIRECTION | PROPAGATION | PR vs. RP INTERVALS | VENTR. RATE vs. UPPER R | ATRIAL RATE vs. UPPER R | VENTR. RATE vs. LOWER R | ATRIAL RATE vs. LOWER R |
|---|---|---|---|---|---|---|---|
| SINUS RHYTHM | | | | | | | |
| STABLE SINUS RHYTHM | ANTEROGRADE | CONSTANT | LESS | LOWER | LOWER | HIGHER | HIGHER |
| AND PHYSIOL. SIN. ARRHYTM | ANTERO | CONSTANT | LESS | LOWER | LOWER | HIGHER | HIGHER |
| A-V BLOCK | | | | | | | |
| AND SINUS RHYTHM | ANTERO | CONSTANT | <,=,> | LOWER | LOWER | LO,=,HI | HIGHER |
| AND ATR. FIBRILLATION | BOTH | VARIABLE | <,=,> | LOWER | LO,=,HI | LO,=,HI | HIGHER |
| AND ATR. FLUTTER | BOTH | CONSTANT | <,=,> | LOWER | HIGHER | LO,=,HI | HIGHER |
| AND ATR. TACHYCARDIA | BOTH | CONSTANT | <,=,> | LOWER | HIGHER | LO,=,HI | HIGHER |
| AND ATR. REENTRY | BOTH | CONSTANT | <,=,> | LOWER | LOWER | LO,=,HI | HIGHER |
| ATRIAL ARRHYTHMIAS | | | | | | | |
| ATRIAL FIBRILLATION | BOTH | VARIABLE | <,=,> | LO,=,HI | LO,=,HI | HIGHER | HIGHER |
| ATRIAL FLUTTER | BOTH | CONSTANT | <,=,> | LO,=,HI | HIGHER | HIGHER | HIGHER |
| ATRIAL TACHYCARDIA | BOTH | CONSTANT | <,=,> | LO,=,HI | HIGHER | HIGHER | HIGHER |
| ATRIAL REENTRY | BOTH | CONSTANT | LESS | LO,=,HI | LO,=,HI | HIGHER | HIGHER |
| ATRIAL PREMAT. CONTR. | BOTH | VARIABLE | LESS | LO,=,HI | LO,=,HI | HIGHER | HIGHER |
| SUPRAVENTR. TACHYCARDIA | | | | | | | |
| A-V NODE REENTRY | RETROGRADE | CONSTANT | <,=,> | HIGHER | HIGHER | HIGHER | HIGHER |
| LEFT KENT REENTRY | BOTH | CONSTANT | MORE | HIGHER | HIGHER | HIGHER | HIGHER |
| RIGHT KENT REENTRY | RETRO | CONSTANT | MORE | HIGHER | HIGHER | HIGHER | HIGHER |
| KENT REENTRY AND ATR. FIB. | BOTH | VARIABLE | <,=,> | HIGHER | HIGHER | HIGHER | HIGHER |
| VENTR. PREMAT. BEATS | | | | | | | |
| AND SINUS RHYT. AND V-A=0 | ANTERO | CONSTANT | LESS | LO,=,HI | LOWER | HIGHER | HIGHER |
| AND SINUS RHYT. AND V-A PRES | BOTH | VARIABLE | <,=,> | LO,=,HI | LO,=,HI | HIGHER | HIGHER |
| AND ATRIAL FIBRILLATION | BOTH | VARIABLE | <,=,> | LO,=,HI | LO,=,HI | HIGHER | HIGHER |
| AND ATR. FLUTTER AND V-A=0 | BOTH | CONSTANT | <,=,> | LO,=,HI | HIGHER | HIGHER | HIGHER |
| AND ATR.FLUTTER AND V-A PRES | BOTH | VARIABLE | <,=,> | LO,=,HI | HIGHER | HIGHER | HIGHER |
| AND ATR.TACHYC. AND V-A=0 | BOTH | CONSTANT | <,=,> | LO,=,HI | HIGHER | HIGHER | HIGHER |
| AND ATR.TACHYC. AND V-A PRES | BOTH | VARIABLE | <,=,> | LO,=,HI | HIGHER | HIGHER | HIGHER |
| AND ATR.REENTRY AND V-A=0 | BOTH | CONSTANT | <,=,> | LO,=,HI | LO,=,HI | HIGHER | HIGHER |
| AND ATR. REENTRY AND V-A PRES. | BOTH | VARIABLE | <,=,> | LO,=,HI | LO,=,HI | HIGHER | HIGHER |

FIG. 11A

| VENTRIC. TACHYCARDIA | | | ANALYSIS OF CARDIAC RHYTHMS | | | | |
|---|---|---|---|---|---|---|---|
| AND SINUS RHYT. AND V-A=0 | ANTERO | CONSTANT | <,=,> | HIGHER | LOWER | HIGHER | HIGHER |
| AND SINUS RHYT. AND V-A PRES | BOTH | VARIABLE | <,=,> | HIGHER | LO,=, HI | HIGHER | HIGHER |
| AND ATR. FIBRILLATION | BOTH | VARIABLE | <,=,> | HIGHER | LO,=, HI | HIGHER | HIGHER |
| AND ATR. FLUTTER AND V-A=0 | BOTH | CONSTANT | <,=,> | HIGHER | HIGHER | HIGHER | HIGHER |
| AND ATR. FLUTTER AND V-A PRES | BOTH | VARIABLE | <,=,> | HIGHER | HIGHER | LO, =, HI | HIGHER |
| AND ATR.TACHYC. AND V-A=0 | BOTH | CONSTANT | <,=,> | HIGHER | HIGHER | LO, =, HI | HIGHER |
| AND ATR.TACHYC. AND V-A PRES | BOTH | VARIABLE | <,=,> | HIGHER | HIGHER | LO, =, HI | HIGHER |
| AND ATR.REENTRY AND V-A=0 | BOTH | CONSTANT | <,=,> | HIGHER | LO, =, HI | LO, =, HI | HIGHER |
| AND ATR.REENTRY AND V-A PRES | BOTH | VARIABLE | <,=,> | HIGHER | LO, =, HI | | HIGHER |
| P M TACHYCARDIA | RETRO | CONSTANT | <,=,> | LO, =, HI | LO, =, HI | | |
| SLOW VENTR.TACH.(AIVR) | | | | | | | |
| AND SINUS RHYT. AND V-A=0 | ANTERO | CONSTANT | <,=,> | LOWER | LOWER | HIGHER | HIGHER |
| AND SINUS RHYT. AND V-A PRES | BOTH | VARIABLE | <,=,> | LOWER | LOWER | HIGHER | HIGHER |
| AND ATR. FIBRILLATION | BOTH | VARIABLE | <,=,> | LOWER | LO, =, HI | HIGHER | HIGHER |
| AND ATR. FLUTTER AND V-A=0 | BOTH | CONSTANT | <,=,> | LOWER | HIGHER | HIGHER | HIGHER |
| AND ATR.FLUTTER AND V-A PRES | BOTH | VARIABLE | <,=,> | LOWER | HIGHER | HIGHER | HIGHER |
| AND ATR.TACHYC. AND V-A=0 | BOTH | CONSTANT | <,=,> | LOWER | HIGHER | HIGHER | HIGHER |
| AND ATR.TACHYC. AND V-A=PRES | BOTH | VARIABLE | <,=,> | LOWER | HIGHER | HIGHER | HIGHER |
| AND ATR.REENTRY AND V-A=PRES | BOTH | CONSTANT | <,=,> | LOWER | LO, =, HI | LO, =, HI | HIGHER |
| AND ATR.REENTRY AND V-A PRES | BOTH | VARIABLE | <,=,> | LOWER | LO, =, HI | LO, =, HI | HIGHER |
| VENTR. FIBRILLATION | | | | | | | |
| AND SINUS RHYT. AND V-A=0 | ANTERO | CONSTANT | <,=,> | HIGHER | LOWER | HIGHER | HIGHER |
| AND SINUS RHYT. AND V-A PRES | BOTH | VARIABLE | <,=,> | HIGHER | LO, =, HI | HIGHER | HIGHER |
| AND ATR. FIBRILLATION | BOTH | VARIABLE | <,=,> | HIGHER | LO, =, HI | HIGHER | HIGHER |
| AND ATR.FLUTTER AND V-A=0 | BOTH | CONSTANT | <,=,> | HIGHER | HIGHER | HIGHER | HIGHER |
| AND ATR.FLUTTER AND V-A PRES | BOTH | VARIABLE | <,=,> | HIGHER | HIGHER | HIGHER | HIGHER |
| AND ATR.TACHYC. AND V-A=0 | BOTH | CONSTANT | <,=,> | HIGHER | HIGHER | HIGHER | HIGHER |
| AND ATR.TACHYC. AND V-A PRES | BOTH | VARIABLE | <,=,> | HIGHER | HIGHER | HIGHER | HIGHER |
| AND ATR.REENTRY AND V-A=0 | BOTH | CONSTANT | <,=,> | HIGHER | LO, =, HI | HIGHER | HIGHER |
| AND ATR.REENTRY AND V-A PRES | BOTH | VARIABLE | <,=,> | HIGHER | LO, =, HI | HIGHER | HIGHER |
| JUNCTIONAL ARRHYTHMIAS | | | | | | | |
| JUNCT. PREMAT. CONTRAC. | RETRO | VARIABLE | <,=,> | LO, =, HI | LO, =, HI | HIGHER | HIGHER |
| JUNCT. TACHYCARDIA | RETRO | CONSTANT | <,=,> | LO, =, HI | LO, =, HI | HIGHER | HIGHER |

FIG. IIB

| P COUNT vs R COUNT | VENTR. RHYTHM | ATRIAL RHYTHM | TACHYCARDIA ONSET | SITE OF PREMATURITY | AV CONDUCTION |
|---|---|---|---|---|---|
| EQUAL | REGULAR | REGULAR | | 0 | 0 1 TO 1 |
| EQUAL | IRREGULAR | IRREGULAR | | | 0 1 TO 1 |
| | | | | | |
| P > R | REGUL OR IRREGUL | REGULAR | | 0 | 0 >1 TO 1 |
| P > R | REGULAR | IRREGULAR | ATR:PROGR. OR ABRUPT  VENTR:0 | ATRIAL | >1 TO 1 |
| P > R | REGULAR | REGULAR | ATR:ABRUPT  VENTR:0 | ATRIAL | >1 TO 1 |
| P > R | REGULAR | REGULAR | ATR:ABRUPT  VENTR:0 | ATRIAL | >1 TO 1 |
| P > R | REGULAR | REGULAR | ATR:ABRUPT  VENTR:0 | ATRIAL | >1 TO 1 |
| | | | | | |
| P > R | IRREGULAR | IRREGULAR | ATR AND VENTR : PROGR. OR ABRUPT | ATRIAL | >1 TO 1 |
| P > R | BOTH | REGULAR | ATR :ABRUPT  VENTR:PROGR OR ABRUPT | ATRIAL | >1 TO 1 |
| P = OR > R | BOTH | REGULAR | ATR :ABRUPT  VENTR:PROGR OR ABRUPT | ATRIAL | > OR = 1 TO 1 |
| P = OR > R | REGULAR | REGULAR | ATR. AND VENTR: ABRUPT | ATRIAL | > OR = 1 TO 1 |
| P = OR > R | IRREGULAR | IRREGULAR | | 0 ATRIAL | > OR = 1 TO 1 |
| | | | | | |
| EQUAL | REGULAR | REGULAR | ATR. AND VENTR: ABRUPT | ATRIAL OR VENTR | 1 TO 1 |
| EQUAL | REGULAR | REGULAR | ATR. AND VENTR: ABRUPT | ATRIAL OR VENTR | 1 TO 1 |
| EQUAL | REGULAR | REGULAR | ATR. AND VENTR: ABRUPT | ATRIAL OR VENTR | 1 TO 1 |
| P > R | IRREGULAR | IRREGULAR | ATR AND VENTR:PROGR OR ABRUPT | ATRIAL OR VENTR | >1 TO 1 |
| | | | | | |
| P < OR = R | IRREGULAR | REGULAR | | 0 VENTR | 1 TO 1 IN SR |
| P = R | IRREGULAR | BOTH | | 0 VENTR | 1 TO 1 IN SR |
| P > R | IRREGULAR | IRREGULAR | ATR:PROGR OR ABRUPT  VENTR:0 | BOTH | >1 TO 1 |
| P > R | BOTH | REGULAR | ATR:ABRUPT  VENTR:0 | BOTH | >1 TO 1 |
| P > R | BOTH | BOTH | ATR:ABRUPT  VENTR:0 | BOTH | >1 TO 1 |
| P < OR = R | BOTH | REGULAR | ATR:ABRUPT  VENTR:0 | BOTH | > OR = 1 TO 1 |
| P < OR > R | BOTH | BOTH | ATR:ABRUPT  VENTR:0 | BOTH | > OR = 1 TO 1 |
| P < OR > R | BOTH | REGULAR | ATR:ABRUPT  VENTR:0 | BOTH | > OR = 1 TO 1 |
| P < OR > R | BOTH | BOTH | ATR:ABRUPT  VENTR:0 | BOTH | > OR = 1 TO 1 |

FIG. 11C

ANALYSIS OF CARDIAC RHYTHMS

| | | | | | | |
|---|---|---|---|---|---|---|
| P > R | | REGULAR | REGULAR | ATR: 0 | VENTR: ABRUPT | NO ANALYSIS |
| P < OR = R | | REGULAR | BOTH | ATR: 0 | VENTR: ABRUPT | NO ANALYSIS |
| P < OR > R | | REGULAR | IRREGULAR | ATR:PROGR OR ABRUPT | VENTR: ABRUPT | NO ANALYSIS |
| P > R | | REGULAR | REGULAR | ATR:ABRUPT | VENTR: ABRUPT | NO ANALYSIS |
| P > R | | REGULAR | BOTH | ATR:ABRUPT | VENTR: ABRUPT | NO ANALYSIS |
| P < OR = R | | REGULAR | REGULAR | ATR:ABRUPT | VENTR: ABRUPT | NO ANALYSIS |
| P < OR = R | | REGULAR | BOTH | ATR:ABRUPT | VENTR: ABRUPT | NO ANALYSIS |
| P < OR > R | | REGULAR | REGULAR | ATR:ABRUPT | VENTR: ABRUPT | NO ANALYSIS |
| P < OR > R | | REGULAR | BOTH | ATR:ABRUPT | VENTR: ABRUPT | NO ANALYSIS |
| P < OR > R | | REGULAR | REGULAR | ATR:ABRUPT | VENTR: ABRUPT | 1 TO 1 |
| P < R | | REGULAR | REGULAR | ATR: 0 | VENTR: ABRUPT | NO ANALYSIS |
| P < OR = R | | REGULAR | BOTH | ATR: 0 | VENTR: ABRUPT | NO ANALYSIS |
| P < OR = R | | REGULAR | IRREGULAR | ATR:PROGR OR ABRUPT | VENTR: ABRUPT | NO ANALYSIS |
| P > R | | REGULAR | REGULAR | ATR:ABRUPT | VENTR: ABRUPT | NO ANALYSIS |
| P > R | | REGULAR | BOTH | ATR:ABRUPT | VENTR: ABRUPT | NO ANALYSIS |
| P < OR = R | | REGULAR | REGULAR | ATR:ABRUPT | VENTR: ABRUPT | NO ANALYSIS |
| P < OR = R | | REGULAR | BOTH | ATR:ABRUPT | VENTR: ABRUPT | NO ANALYSIS |
| P < OR > R | | REGULAR | REGULAR | ATR:ABRUPT | VENTR: ABRUPT | NO ANALYSIS |
| P < OR > R | | REGULAR | BOTH | ATR:ABRUPT | VENTR: ABRUPT | NO ANALYSIS |
| P < R | | IRREGULAR | REGULAR | ATR: 0 | VENTR: ABRUPT | NO ANALYSIS |
| P < R | | IRREGULAR | BOTH | ATR: 0 | VENTR: ABRUPT | NO ANALYSIS |
| P < OR > R | | IRREGULAR | IRREGULAR | ATR:PROGR OR ABRUPT | VENTR: ABRUPT | NO ANALYSIS |
| P < OR = R | | IRREGULAR | REGULAR | ATR:ABRUPT | VENTR: ABRUPT | NO ANALYSIS |
| P < OR = R | | IRREGULAR | BOTH | ATR:ABRUPT | VENTR: ABRUPT | NO ANALYSIS |
| P < OR = R | | IRREGULAR | REGULAR | ATR:ABRUPT | VENTR: ABRUPT | NO ANALYSIS |
| P < OR = R | | IRREGULAR | BOTH | ATR:ABRUPT | VENTR: ABRUPT | NO ANALYSIS |
| P < R | | IRREGULAR | REGULAR | ATR:ABRUPT | VENTR: ABRUPT | NO ANALYSIS |
| P < R | | IRREGULAR | BOTH | ATR:ABRUPT | VENTR: ABRUPT | NO ANALYSIS |
| P = R | | IRREGULAR | IRREGULAR | | 0 | NO ANALYSIS |
| P = R | | REGULAR | REGULAR | ATR:ABRUPT | VENTR: ABRUPT | ATRIAL OR VENTR | NO ANALYSIS |

FIG. 11D

METHOD AND APPARATUS USING WINDOWS AND AN INDEX VALUE FOR IDENTIFYING CARDIC ARRHYTHMIAS

FIELD OF THE INVENTION

This invention relates generally to implanted medical devices and, more particularly, relates to a physiological waveform morphology discrimination method and apparatus for use in identifying cardiac arrhythmias and adjusting the operation of the medical device accordingly.

BACKGROUND OF THE INVENTION

Early automatic tachycardia detection systems for automatic implantable cardioverter/defibrillators relied upon the presence or absence of electrical and mechanical heart activity (such as intramyocardial pressure, blood pressure, impedance, stroke volume or heart movement) and/or the rate of the electrocardiogram. For example, the 1961 pamphlet by Dr. Fred Zacouto, Paris, France, entitled, "Traitement D'Urgence des Differents Types de Syncopes Cardiaques du Syndrome de Morgangni-Adams-Stokes" (National Library of Medicine) describes an automatic pacemaker and defibrillator responsive to the presence or absence of the patient's blood pressure in conjunction with the rate of the patient's electrocardiogram. Later detection algorithms proposed by Satinsky, "Heart Monitor Automatically Activates Defibrillator," Medical Tribune, 9, No. 91:3, Nov. 11, 1968, and Schuder et al "Experimental Ventricular Defibrillation with an Automatic and Completely Implanted System," Transactions American Society for Artificial Internal Organs, 16:207, 1970, automatically detected and triggered defibrillation when the amplitude of the R-wave of the electrocardiogram fell below a predetermined threshold over a predetermined period of time. The initial system proposed by Mirowski et al in U.S. Pat. No. Re 27,757, which similarly relied upon the decrease in the amplitude of a pulsatile right ventricular pressure signal below a threshold over a predetermined period of time, was abandoned by Mirowski et al in favor of the rate and/or probability density function morphology discrimination as described in Mower et al, "Automatic Implantable Cardioverter -Defibrillator Structural Characteristics," PACE, Vol. 7, November–December 1984, Part 11, pp. 1331–1334. Others have suggested the use of high rate plus acceleration of rate or "onset" (U.S. Pat. No. 4,384,585) with sustained high rate and rate stability (U.S. Pat. No. 4,523,595).

Very generally, the systems that depend upon the aforementioned criteria are capable of discriminating tachyarrhythmia in greater or lesser degree from normal heart rhythm but have difficulty discriminating sinus or other supraventricular tachycardias from malignant, pathologic ventricular tachycardias, resulting in the delivery of inappropriate cardiac electrical stimulation therapies.

As stated in the article "Automatic Tachycardia Recognition" by R. Arzbaecher et al (PACE, May–June 1984, pp. 541-547), antitachycardia pacemakers that were undergoing clinical studies prior to the publication of that article detected tachycardia by sensing a high rate in the chamber to be paced. The specific criteria to be met before pace termination was to be attempted involved a comparison of the detected rate to a preset threshold, such as 150 beats per minute (400 millisecond cycle length) for a pre-selected number of beats. As stated above, other researchers had suggested the rate of change of rate or suddenness of onset, rate stability and sustained high rate as additional criteria to distinguish sinus tachycardias from malignant tachycardias. Arzbaecher et al proposed in their article an algorithm implemented in a microprocessor based implantable device employing both atrial and ventricular rate detection via separate bipolar leads in order to detect the M and VA, or VV and AV intervals (or "cycle lengths") against threshold intervals in order to distinguish pace-terminable and nonpace-terminable tachycardias. Arzbaecher et al introduced the concept of employing a single atrial extra stimulus to distinguish sinus tachycardia from 1:1 paroxysmal tachycardia in order to determine whether a ventricular response would be elicited. An atrial extra stimulus was delivered in late diastole (80 milliseconds premature), and the ventricular response, if appearing early as well, indicated that the patient was in sinus rhythm. However, in pace-terminable tachycardias, such as AV reentrant and ventricular with VA conduction tachycardia, the ventricular response would not occur early (indicating that the atrial and ventricular rhythms were disassociated) and the ventricular rhythm would be unperturbed.

Other proposals for employing atrial and ventricular detection and interval comparison are set forth in The Third Decade of Cardiac Pacing: Advances in Technology in Clinical Applications, Part III, Chapter 1, "Necessity of Signal Processing in Tachycardia Detection" by Furman et al (edited by S. Barold and J. Mugica, Future Publications, 1982, pages 265–274) and in the Lehmann U.S. Pat. No. 4,860,749. In these cases also, atrial and ventricular rates or intervals are compared to one another in order to distinguish sinus and pathological tachycardias.

Another approach to the detection of and discrimination between pathologic and sinus or normal tachycardias involves the comparison of current electrogram morphologies to a stored library of morphologies in the manner shown for example in the U.S. Pat. No. 4,523,595. In such systems, the suspect electrograms are continuously digitized and compared against the reference digitized electrograms to find the closest fit and diagnose the suspect rhythm.

The aforementioned discussion reflects the development in the art of the detection and discrimination of spontaneously occurring atrial and ventricular tachycardias. As is apparent, however, in spite of the many and varied approaches which have been tried, there still remains a need for a reliable method and apparatus for identifying cardiac arrhythmias and providing an appropriate electrical stimulation therapy.

SUMMARY OF THE INVENTION

It is an object of the present invention to identify cardiac arrhythmias.

It is a further object of the present invention to provide a method and apparatus for identifying cardiac arrhythmias and for providing appropriate therapies for the treatment thereof.

These and other objects are accomplished through the present invention which provides a method and apparatus for identifying cardiac arrhythmias. In the preferred embodiment the invention is embodied in an implantable pulse generator. The IPG features a system to analyze the sensed ECG. The system utilizes an algorithm able to quantify continuously the sensed cardiac rhythm. The algorithm features essentially two parts, a pre-diagnostic program ( "PDP"), which is able to discriminate up to 95% of all sensed rhythms, and a diagnostic program ( "DP"), which is able to discriminate the remaining sensed rhythms. The pre-diagnostic program is relatively quicker and draws less energy as compared to the diagnostic program. The pre-diagnostic program functions by regularly measuring the dv/dt of the sensed ECG. These values are then converted into an index value to thereby quantify the sensed cardiac rhythm. After any noise is rejected, the algorithm permits an automatic discrimination of normal sinus rhythm from atrial fibrillation, atrial flutter, ventricular tachycardia, ventricular fibrillation and ventricular flutter. In cases where other rhythms are sensed, the algorithm then utilizes the diagnostic program. The diagnostic program compares a series of sensed values from the sensed ECG to a series of references values. Through the various values examined, a discrimination among various arrhythmias is accomplished.

BRIEF DESCRIPTION OF THE DRAWINGS

The present invention may be better understood and appreciated with reference to a detailed description of the specific embodiment of the invention, when read in conjunction with the accompanying drawings, wherein;

FIG. 8 is an example of the operation of the pre-diagnostic program upon a sensed ECG using a high right atrial electrode.

FIG. 9 is a second example of the operation of the pre-diagnostic program upon a sensed ECG using a high right atrial electrode.

FIG. 10 depicts a set of dv/dt index values corresponding to particular types of tachyarrhythmias.

FIGS. 11 and 11A–11D are an illustration of the matrix of values utilized in the diagnostic program.

Figure 1:
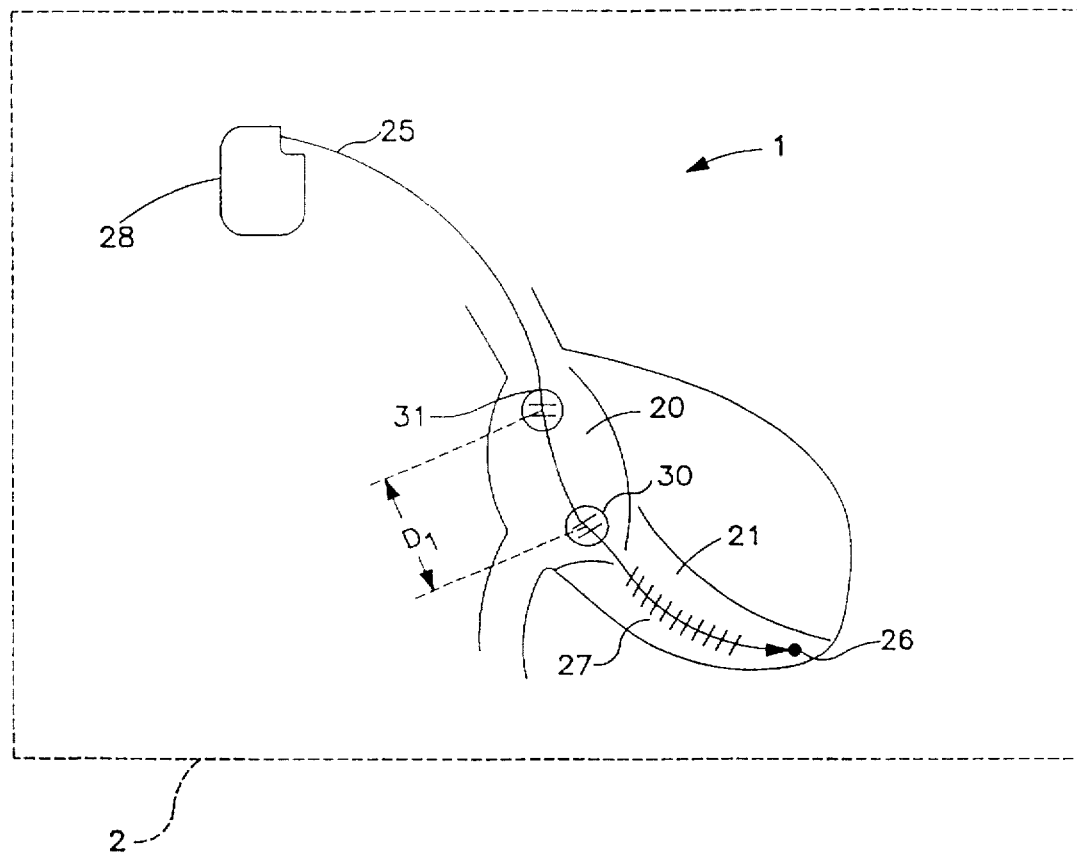
FIG. 1 is a view of a device according to the present invention implanted within a patient.

It should be understood the drawings are not necessarily to scale.

DETAILED DESCRIPTION OF THE INVENTION

An understanding of the operational modes of the first embodiment of the present invention is facilitated by a brief discussion of the physiology of the heart and the theoretical mechanisms of cardiac tachyarrhythmias.

The normal pumping action of the heart results from highly organized electrical activity in the cardiac tissue. Each natural spontaneous heart beat begins with an electrical discharge from the sinoatrial node (S-A) located in the right atrium of the heart. This electrical impulse is conducted through tissues which results in the progressive depolarization of the atrial tissue causing it to contract. The contraction forces blood from the atrium through the heart valves into the ventricles. The electrical impulse from the atrium is communicated to the ventricles through the atrio-ventricular node (A-V), which is located on the septal wall dividing the right and left heart. The electrical signal is delayed in this conductive mode for approximately 0.15 seconds and is then transmitted through the His bundle and its branches to the Purkinje fibers which discharge ventricular muscle, causing the ventricles to contract in an organized fashion and pump blood throughout the body. In the healthy heart, this normal sinus rhythm may be repeated between 60 and 120 times per minute. In the diseased heart, however, a number of arrhythmias may occur which disrupt this normal activity. The type of arrhythmias are divided into two groups: tachyarrhythmias, which are generally characterized by heart rates faster than normal, and bradyarrhythmias, which are characterized by heart rates lower than normal.

The characterization and origin of a tachyarrhythmia is of practical significance since the success of drug treatment of such disorders depends to a great degree on the accurate determination of their origin and cause. In contrast, when cardioversion is selected to treat these disorders, the characterization and origin of the arrhythmia is of less significance. For example, it has been shown that transthoracic DC electrical shock can successfully terminate many different types of tachyarrhythmias. See, for example, Cardioversion, B. Lown, Med. Ann. D. C., 38:543, 1969. However, in an implantable device where power source energy and patient tolerance to repeated cardioversion/defibrillation shocks are both limited, it is necessary to draw fine distinctions between types of tachyarrhythmias and to treat the detected tachyarrhythmias with the lowest energy, least painful electrical stimulation, and potentially most effective, therapies. Thus, it is desirable to terminate tachyarrhythmias whenever possible by low energy painless pacing stimuli and, if necessary, increase the aggressiveness of the therapy if the arrhythmia is not pace-terminable or accelerates to a nonpace-terminable arrhythmia.

Conversely, it is desirable to immediately discriminate the nonpace-terminable and life threatening ventricular fibrillation and unstable ventricular tachycardia, and immediately treat those arrhythmias with cardioversion/defibrillation shock therapies.

Tachyarrhythmias may be characterized further by their location of origin. For example, the origin of supraventricular tachyarrhythmias is in the atria; and its maintenance involves the atria and sometimes ventricles. Ventricular tachyarrhythmias originate and are maintained within the ventricles and sometimes conduct to the atria by a retrograde conduction pathway. A separate group of tachyarrhythmias are called flutter or fibrillation. Flutter is generally characterized by rapid, organized heart activity and, when involving the ventricles, low cardiac output. Fibrillation is characterized by highly disorganized electrical activity that results in virtually no cardiac output when it involves the ventricles. In some patients there may be a progression from an organized tachycardia to fibrillation which will lead to death if the site of the fibrillation is the ventricles. In many patients, ventricular tachycardia precedes the onset of ventricular fibrillation; and if the former can be terminated, generally with small amounts of energies, the latter can be prevented. Some patients exhibit chronic atrial flutter or fibrillation which may be debilitating but does not cause death, and other patients exhibit occasional or paroxysmal attacks of ventricular tachycardias which require cardioversion. See, for example, "Cardiac Arrhythmias," in Current Diagnosis, W. B. Saunders Co., 1977, pp. 377–396, by Douglas P. Zipes, M.D.

Ventricular tachycardias can be converted to sinus rhythm by the application of cardioversion shock or by the application of pacing energy electrical stimulation including rate adaptive or orthorhythmic stimulation as described first in Zacouto U.S. Pat. No. 3,857,399, overdrive stimulation, burst overdrive stimulation rate scanning or any of the other known pacing therapies as described, for example, in Fisher et al, "Implantable Pacers for Tachycardia Termination: Stimulation Techniques and Long-Term Efficacy", PACE, Vol.9, November–December 1986, Part II, pp. 1325–1333. As a general proposition, it is preferable to convert ventricular tachycardias, if possible, to sinus rhythm by application of lower energy stimulation in order to conserve energy of the power sources of the implantable device as well as to maintain patient comfort. Many patients cannot tolerate the pain associated with cardioversion or defibrillation shock therapies leading to dread of the implanted cardioverter/defibrillator. Thus, it is desirable to further distinguish pace-terminable from nonpace terminable ventricular tachycardias and program the implanted device to first attempt to restore sinus rhythm through the application of programmed pacing energy therapies of one or more of the types described above.

Referring now to FIG. 1, there is shown a diagrammatic representation of device 1 according to the present invention implanted within a patient 2. As seen device 1 features an implantable pulse generator 28 and lead 25. The lead 25 has a bipolar pacing electrode 26 positioned at the distal end thereof. Although a bipolar pacing electrode 26 is preferred, a unipolar pacing electrode may also be used, as is well known in the art. Lead is positioned in the right ventricle for good contact with the heart wall, and the lead may include tines or other anchoring means for holding the pacing lead in position. Lead 25 further features defibrillation electrode 27.

As illustrated, when the distal portion of the lead is positioned in the ventricle 21, a proximal portion is positioned in the atrium 20. The proximal end of the lead has a connector (not shown) for connection to the implantable pulse generator 28. As is common in the art, a conducting wire or wires extend the length of the lead for electrically connecting the distal electrode or electrodes to the connector, whereby stimulus pulses may be transferred through to the distal end and signals sensed in the ventricle may be transmitted back to the pacemaker or other receiving instrument.

In the invention as shown, the floating portion of the lead which passes through the atrium has a pair of bipole electrodes 30, 31. As used herein, the term "bipole" refers to a pair of electrodes. In this case, the lead 25 is floating in the atrial region, i.e., it is not pressed against the atrial wall, except by chance, such that bipoles 30, 31 are floating relative to the chamber walls. In the preferred embodiment bipole electrodes 30, 31 are fashioned according to the teachings of U.S. Pat. No. 5,172,694 of Flammang, et al., incorporated herein by reference.

Bipoles 30 is in the lower portion of the atrium near the tricuspid valve (between the atrium and the ventricle) while bipole 31 is in the upper portion of the atrium. Each bipole 30, 31 is preferably a whole-ring electrode. The whole-ring bipole is suitably a conventional arrangement of electrode rings which circle the outer circumference of the generally cylindrical lead 25. Typically the surface area of each ring of the whole-ring bipole 30 is about 10 sq. mm., but preferably greater than 5 sq. mm. It has been found that it is important, also, that the areas of the respective electrodes are balanced, i.e., about equal. While the term "whole-ring" generally refers to rings which encompass all 360 degrees of the lead circumference, as used in the claims defining this invention "whole-ring" refers to any ring which circles at least 75% of the circumference. As illustrated in FIG. 1, the whole-ring bipole is floating, i.e., there is no mechanism for anchoring the bipole against the atrial wall. Although each electrode 30, 31 is preferable a whole ring, each may be fashioned in any other suitable configuration, such as a split-ring, as seen in the aforementioned U.S. Patent of Flammang, et al. Each bipole has a pair of wires (not shown) connecting to IPG 28.

In practice, a physician positions the lead so that the distal electrode 26 is positioned in the ventricle for good ventricular pacing. Bipole 30 is positioned sufficiently proximal, i.e., about 90–110 cm from the distal tip, so that it lies within the atrium, although within the lower atrium near the tricuspid valve.

In practice, the distance D between the upper atrial and lower atrial bipoles is established to optimize sensing of the P-wave timing and direction. A particular use of the atrial lead of this invention is to obtain separate sensings of P-waves at different locations to determine the conduction time and direction of atrial depolarization, i.e., to determine whether the P-wave is antegrade or retrograde. For this purpose, the bipole separation D1 is suitably in the range of about 15 to 60 mm.

Figure 2:
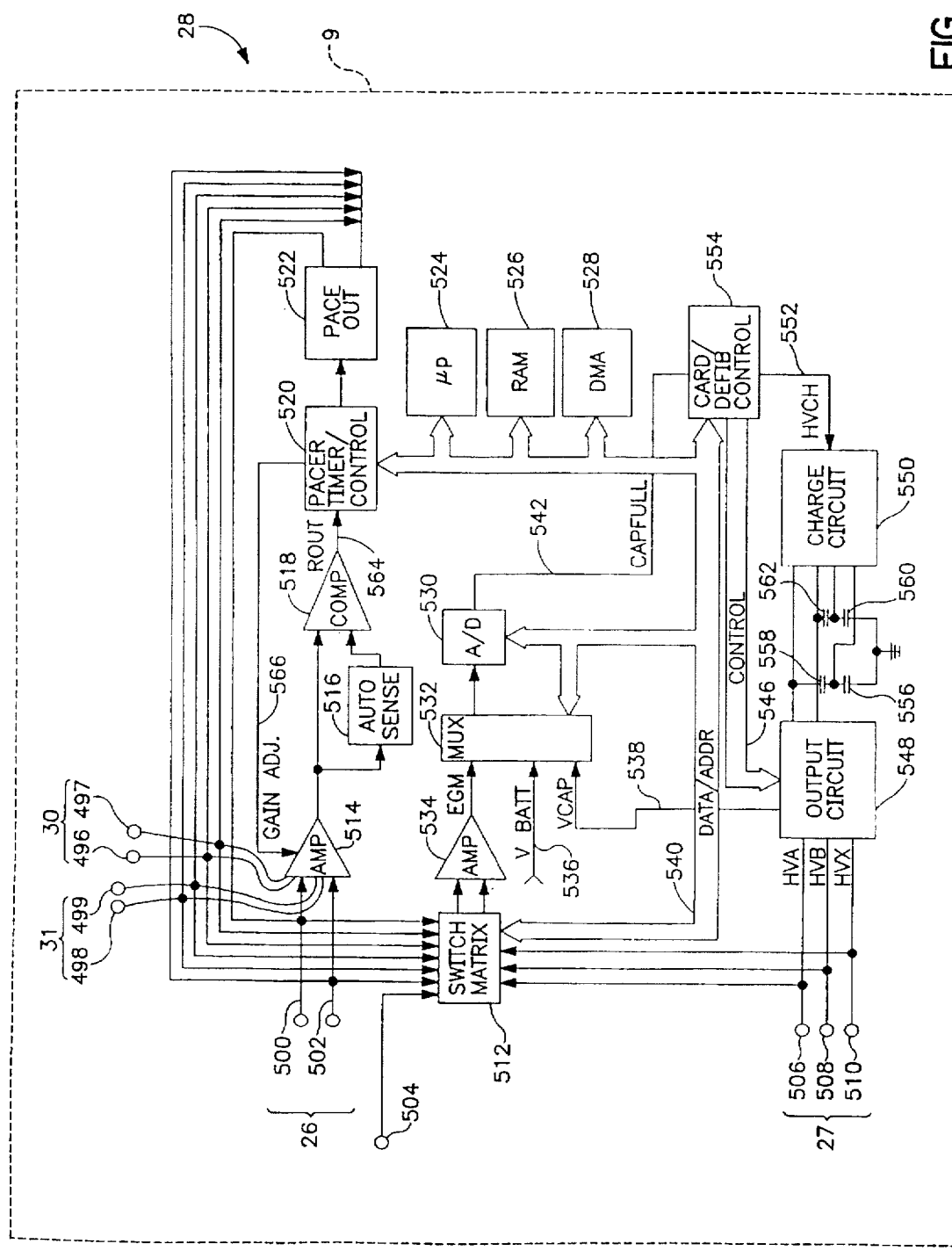
FIG. 2 is a functional schematic diagram of a pulse generator used in the system of the present invention.

Turning now to FIG. 2, which depicts a functional schematic diagram of an implantable pulse generator in which the present invention may usefully be practiced. This diagram should be taken as exemplary of the type of device in which the invention may be embodied, and not as limiting, as it is believed that the invention may usefully be practiced in a wide variety of device implementations, including devices having functional organization similar to any of the implantable pacemaker/defibrillator /cardioverters presently being implanted for clinical evaluation in the United States. The invention is also believed practicable in conjunction with implantable pacemaker/cardioverters/ defibrillators as disclosed in prior U.S. Pat. No. 4,548,209, issued to Wielders, et al. on Oct. 22, 1985, U.S. Pat. No. 4,693,253, issued to Adams et al. on Sep. 15, 1987, U.S. Pat. No. 4,830,006, issued to Haluska et al. on May 6, 1989 and U.S. Pat. No. 4,949,730, issued to Pless et al. on Aug. 21, 1990, all of which are incorporated herein by reference in their entireties.

As seen IPG 28 is enclosed by hermetic enclosure 9 to protect the components from body fluids, as is well known in the art. The device is illustrated as being provided with eight electrodes: 496, 497, 498, 499, 500, 502, 504, 506, 508 and 510. Electrodes 496 and 497 are a pair of ring electrodes which make-up bipole electrode 30, preferable located in the lower atrium. Electrodes 498 and 499 are a pair of ring electrodes which make-up bipole electrode 31, preferable located in the upper atrium. Electrodes 500 and 502 may be a pair of endocardial electrodes located in the ventricle, mounted to a transvenous lead. Electrode 504 may correspond to a remote, indifferent electrode located on the housing of the implantable pacemaker/cardioverter/ defibrillator. Electrodes 506, 508 and 510 may correspond to the large surface area defibrillation electrodes located on ventricular, coronary sinus, superior vena cava or subcutaneous leads, to electrodes located on or part of the device housing or to epicardial defibrillation electrodes.

Electrodes 500 and 502 are shown as hard-wired to the R-wave detector circuit, comprising band-pass filter circuit 514, auto threshold circuit 516 for providing an adjustable sensing threshold as a function of the measured R-wave amplitude and comparator 518. A signal is generated on R-out line 564 whenever the signal sensed between electrodes 500 and 502 exceeds the present sensing threshold defined by the auto threshold circuit 516. As illustrated, the gain on the band pass amplifier 514 is also adjustable by means of a signal from the pacer timing and control circuitry 520 on GAIN ADJ line 566.

The operation of this R-wave detection circuitry may correspond to that disclosed in commonly assigned U.S. Pat. No. 5,118,824, issued to Keimel and incorporated herein by reference in its entirety. However, alternative R-wave detection circuitry such as that illustrated in U.S. Pat. No. 4,819,643, issued to Menken on Apr. 11, 1989 and U.S. Pat. No. 4,880,004, issued to Baker et al. on Nov. 14, 1989, both incorporated herein by reference in their entireties, may also usefully be employed to practice the present invention. The threshold adjustment circuit 516 sets a threshold corresponding to a predetermined percentage of the amplitude of a sensed R-wave, which threshold decays to a minimum threshold level over a period of less than three seconds thereafter, similar to the automatic sensing threshold circuitry illustrated in the article "Reliable R-Wave Detection from Ambulatory Subjects", by Thakor et al., published in Biomedical Science Instrumentation, Vol. 4, pp. 67–72, 1978, incorporated herein by reference in its entirety.

It is preferable that the threshold level not be adjusted in response to paced R-waves, but instead should continue to approach the minimum threshold level following paced R-waves to enhance sensing of low level spontaneous R-waves associated with tachyarrhythmias. The time constant of the threshold circuit is also preferably sufficiently short so that minimum sensing threshold may be reached within 1–3 seconds following adjustment of the sensing threshold equal to 70–80% of the amplitude of a detected spontaneous R-wave. The invention may also be practiced in conjunction with more traditional R-wave sensors of the type comprising a band pass amplifier and a comparator circuit to determine when the band-passed signal exceeds a predetermined, fixed sensing threshold.

Switch matrix 512 is used to select which of the available electrodes are coupled to band pass amplifier 534. Selection of which two electrodes are so coupled is controlled by the microprocessor 524 via data/address bus 540. Signals from the selected electrodes are passed through band-pass amplifier 534 and into multiplexer 532, where they are converted to multi-bit digital signals by A/D converter 530, for storage in random access memory 526 under control of direct memory address circuit 528. Microprocessor 524 analyzes the digitized EGM signal stored in random access memory 526 to determine the width of the stored R-wave or in conjunction with the tachycardia l fibrillation discrimination function discussed below.

Amplifier 534 may be a broad band pass amplifier, having a band pass extending for approximately 0.5 to 200 hertz. The filtered EGM signal from amplifier 534 is passed through multiplexer 532, and digitized in A-D converter circuitry 530. The digitized EGM data is stored in random access memory 526 under control of direct memory address circuitry 528. Preferably, a portion of random access memory 526 is configured as a looping or buffer memory which stores at least the preceding several seconds of the EGM signal.

The data stored in the buffer memory may be optionally employed to perform R-wave width measurements as disclosed in co-pending U.S. patent application Ser. No. 07/867,931, filed Apr. 13, 1992 by Mader et al, incorporated herein by reference in its entirety and/or to perform the ventricular fibrillation/ventricular tachycardia discrimination function disclosed in allowed U.S. Pat. application Ser. No. 07/750,679 filed Aug. 27, 1991 by Bardy et al., also incorporated herein by reference in its entirety. However, the present invention may also readily be practiced in devices which do not include such functions.

The occurrence of an R-wave detect signal on line 564 is communicated to microprocessor 524 via data/address bus 540, and microprocessor 524 notes the time of its occurrence. If the width measurement function is activated, microprocessor 524 waits 100 milliseconds or other physician selected interval following the occurrence of the R-wave detect signal, and thereafter transfers the most recent 200 milliseconds or other physician selected interval of digitized EGM stored in the looping or buffer memory portion of the random access memory circuit 526 to a second memory location, where the contents may be digitally analyzed to determine the width of the stored R-wave. The transferred 200 milliseconds of stored EGM corresponds to a time window extending 100 milliseconds on either side of the R-wave detect signal. Window sizes in any case should be sufficient to allow measurement of the width of detected R-waves. Preferably, the window should expire during the blanking period following R-wave detection. For purposes of the present invention, a sampling rate of 256 Hz with a bandpass of 1.5–100 Hz should be sufficient. As discussed below, the width measurement function is intended to discriminate between high rate sinus rhythms and ventricular tachycardias, and is preferably only applied to R-waves that define the endpoint of an R—R interval within the interval range indicative of tachycardia. Either as a criterion for provisional detection of tachycardia, or after confirmed detection of (slow) tachycardia, the device determines whether a predetermined number or proportion of a series of preceding R-waves, the widths of which have been measured, are greater than a preset threshold value (e.g. at least 8 of the preceding 12 measured R-waves). If the width criterion is satisfied, provisional detection of tachycardia or confirmed detection of slow ventricular tachycardia may optionally occur. If the width criterion is not met, the rhythm is diagnosed as rapid sinus rhythm and no therapy is delivered.

Similar to the width measurement function, if the discriminator function is activated, microprocessor 524 waits 100 milliseconds or other physician selected interval following the occurrence of the R-wave detect signal, and thereafter transfers the most recent 200 milliseconds or other physician selected interval of digitized EGM stored in the looping or buffer memory portion of the random access memory circuit 526 to a second memory location, where the contents may be digitally analyzed. The microprocessor 524 identifies the points in time at which the R-wave detect signal occurs and the point in time at which the 200 ms of stored ECG meets a predetermined criterion (e.g. peak slope). These two stored times, hereafter referred to as the first and second "fiducial points". The cumulative variability of the time intervals separating the occurrence of the first and second fiducial points over a series of beats is used to distinguish fibrillation from high rate ventricular tachycardia.

The time interval d separating the two fiducial points associated with a single detected depolarization wave-front is measured and stored if the detected depolarization occurs at the end of an R—R interval within the interval range associated with fibrillation. In the context of the present invention, following detection of a rhythm which otherwise would be detected as fast VT, the cumulative variability of the value of d over a series of a predetermined number (e.g. 8) of such detected depolarizations is compared to a threshold value set by the physician based on an evaluation of the patient. If the cumulative variability exceeds the threshold, fibrillation is detected. Otherwise, detection of fast ventricular tachycardia is confirmed.

The microprocessor also updates counts related to the R—R intervals previously sensed. The counts, VFEC and VTEC, are incremented on the occurrence of a measured R—R intervals falling within the fibrillation and ventricular tachycardia ranges, respectively, as discussed above. These rate ranges may be defined by the programming stored in the RAM 526.

These counts, along with other stored information reflective of the previous series of R—R intervals such as information regarding the rapidity of onset of the detected short R—R intervals, the stability of the detected R—R intervals, the duration of continued detection of short R—R intervals, the average R—R interval duration and information derived from analysis of stored EGM segments are used to determine whether tachyarrhythmias are present and to distinguish between different types of tachyarrhythmias, as discussed above in conjunction with FIG. 1. Other such detection algorithms for recognizing tachycardias are described in the above cited U.S. Pat. No. 4,726,380, issued to Vollmann, U.S. Pat. No. 4,880,005, issued to Pless et al. and U.S. Pat. No. 4,830,006, issued to Haluska et al., incorporated by reference in their entireties herein. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10,1986, IEEE Computer Society Press, pages 167–170, also incorporated by reference in its entirety herein. However, other criteria may also be measured and employed in conjunction with the present invention.

It is envisioned that onset and stability requirement are optional in a device employing the present invention, and preferably are made available as programmable options, which may be deleted by external programmer command. If included, it is believed preferable that the onset criteria be required to meet prior to initiating counting of VTEC, and that once met, the criterion will remain satisfied until detection of tachycardia termination. Thus, onset is not intended to be a detection criteria required for re-detection of tachycardia, following initial detection. The width criterion, if used, should also be understood to preferably used only in initial detection of tachycardia. This reflects a presumption that following initial detection of ventricular tachycardia, absent a proven return to normal heart rhythm (termination detect), subsequent high ventricular rates should be presumed to be ventricular in origin. The stability criterion, on the other hand, is believed to be appropriate for use both in initial detection of tachycardia and in re-detection of tachycardia.

The remainder of the circuitry is dedicated to the provision of cardiac pacing, cardioversion and defibrillation therapies. The pacer timing/control circuitry 520 includes programmable digital counters which control the basic time intervals associated with VVI mode cardiac pacing, including the pacing escape intervals, the refractory periods during which sensed R-waves are ineffective to restart timing of the escape intervals and the pulse width of the pacing pulses. The durations of these intervals are determined by microprocessor 524, and are communicated to the pacing circuitry 520 via address/data bus 540. Pacer timing/control circuitry also determines the amplitude of the cardiac pacing pulses and the gain of band-pass amplifier, under control of microprocessor 524.

During VVI mode pacing, the escape interval counter within pacer timing/control circuitry 520 is reset upon sensing of an R-wave as indicated by a signal on line 564, and on timeout triggers generation of a pacing pulse by pacer output circuitry 522, which is coupled to electrodes 500 and 502. The escape interval counter is also reset on generation of a pacing pulse, and thereby controls the basic timing of cardiac pacing functions, including anti-tachycardia pacing. The duration of the interval defined by the escape interval timer is determined by microprocessor 524, via data/address bus 540. The value of the count present in the escape interval counter when reset by sensed R-waves may be used to measure the duration of R—R intervals, to detect the presence of tachycardia and to determine whether the minimum rate criteria are met for activation of the width measurement function.

Microprocessor 524 operates as an interrupt driven device, and responds to interrupts from pacer timing/control circuitry 520 corresponding to the occurrence of sensed R-waves and corresponding to the generation of cardiac pacing pulses. These interrupts are provided via data/address bus 540. Any necessary mathematical calculations to be performed by microprocessor 524 and any updating of the values or intervals controlled by pacer timing/control circuitry 520 take place following such interrupts.

In the event that a tachyarrhythmia is detected, and an antitachyarrhythmia pacing regimen is desired, appropriate timing intervals for controlling generation of anti-tachycardia pacing therapies are loaded from microprocessor 524 into the pacer timing and control circuitry 520, to control the operation of the escape interval counter and to define refractory periods during which detection of an R-wave by the R-wave detection circuitry is ineffective to restart the escape interval counter. Similarly, in the event that generation of a cardioversion or defibrillation pulse is required, microprocessor 524 employs the counters in timing and control circuitry 520 to control timing of such cardioversion and defibrillation pulses, as well as timing of associated refractory periods during which sensed R-waves are ineffective to reset the timing circuitry.

In response to the detection of fibrillation or a tachycardia requiring a cardioversion pulse, microprocessor 524 activates cardioversion/defibrillation control circuitry 554, which initiates charging of the high voltage capacitors 556, 558, 560 and 562 via charging circuit 550, under control of high voltage charging line 552. The voltage on the high voltage capacitors is monitored via VCAP line 538, which is passed through multiplexer 532, and, in response to reaching a predetermined value set by microprocessor 524, results in generation of a logic signal on CAP FULL line 542, terminating charging. Thereafter, delivery of the timing of the defibrillation or cardioversion pulse is controlled by pacer timing/control circuitry 520. Any known cardioversion or defibrillation pulse generation circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al., cited above, and in U.S. Pat. No. 4,375,817, issued to Engle et al. Similarly, known circuitry for controlling the timing and generation of anti-tachycardia pacing pulses as described in U.S. Pat. No. 4,577,633, issued to Berkovits et al. on Mar. 25, 1986, U.S.

Pat. No. 4,880,005, issued to Pless et al. on Nov. 14, 1989, U.S. Pat. No. 7,726,380, issued to Vollmann et al. on Feb. 23, 1988 and U.S. Pat. No. 4,587,970, issued to Holley et al. on May 13, 1986 may also be used.

In modern pacemaker/cardioverter/defibrillators, the particular anti-tachycardia and defibrillation therapies are programmed into the device ahead of time by the physician, and a menu of therapies is typically provided. For example, on initial detection of tachycardia, an anti-tachycardia pacing therapy may be selected. On re-detection of tachycardia, a more aggressive anti-tachycardia pacing therapy may be scheduled. If repeated attempts at anti-tachycardia pacing therapies fail, a higher level cardioversion pulse therapy may be selected thereafter. Prior art patents illustrating such pre-set therapy menus of antitachyarrhythmia therapies include the above-cited U.S. Pat. No. 4,830,006, issued to Haluska, et al., U.S. Pat. No. 4,727,380, issued to Vollmann et al. and U.S. Pat. No. 4,587,970, issued to Holley et al. The present invention is believed practicable in conjunction with any of the known anti-tachycardia pacing and cardioversion therapies, and it is believed most likely that the invention of the present application will be practiced in conjunction with a device in which the choice and order of delivered therapies is programmable by the physician, as in current implantable pacemaker/cardioverter/defibrillators.

In addition to varying the therapy delivered following a failed attempt to terminate a tachyarrhythmia, it is also known that adjustment of detection criteria may be appropriate. For example, adjustment may comprise reducing the number of intervals required to detect a tachyarrhythmia to allow a more rapid re-detection or by changing the interval ranges to bias detection towards detection of ventricular fibrillation, for example as disclosed in U.S. Pat. No. 4,971,058, issued to Pless et al and incorporated herein by reference in its entirety.

In the present invention, selection of the particular electrode configuration for delivery of the cardioversion or defibrillation pulses is controlled via output circuit 548, under control of cardioversion/defibrillation control circuitry 554 via control bus 546. Output circuit 548 determines which of the high voltage electrodes 506, 508 and 510 will be employed in delivering the defibrillation or cardioversion pulse regimen, and may also be used to specify a multi-electrode, simultaneous pulse regimen or a multi-electrode sequential pulse regimen. Monophasic or biphasic pulses may be generated. One example of circuitry which may be used to perform this function is set forth in U.S. Pat. No. 5,163,427, issued to Keimel, incorporated herein by reference in its entirety. However, output control circuitry as disclosed in U.S. Pat. No. 4,953,551, issued to Mehra et al. on Sep. 4, 1990 or U.S. Pat. No. 4,800,883, issued to Winstrom on Jan. 31, 1989 both incorporated herein by reference in their entireties, may also be used in the context of the present invention. Alternatively single monophasic pulse regimens employing only a single electrode pair according to any of the above cited references which disclose implantable cardioverters or defibrillators may also be used.

Figure 3:
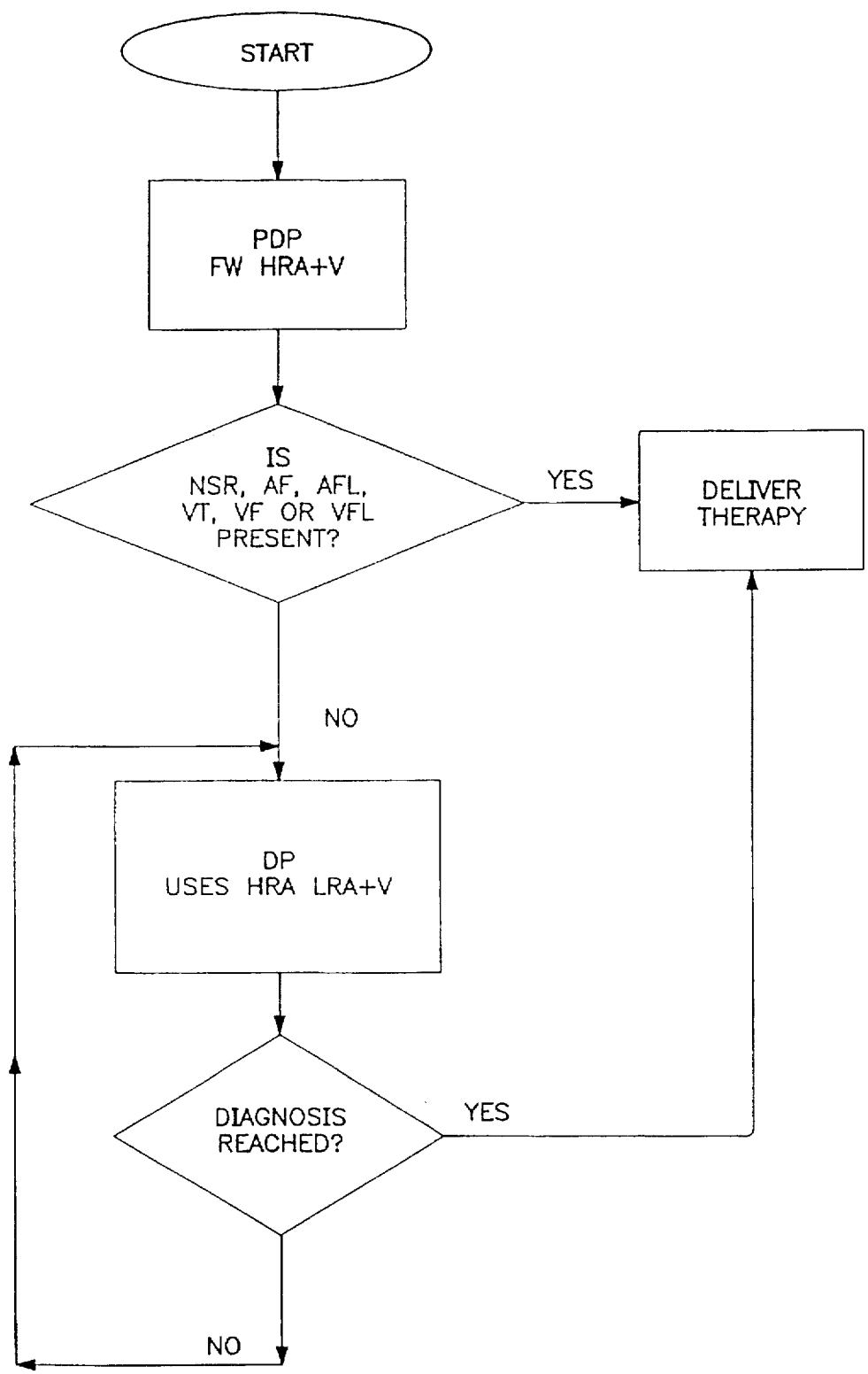
FIG. 3 is a simplified flow chart illustrating the functional operation of the preferred embodiment of the present invention, as embodied in the context of a device illustrated in FIG. 2.

Turning now to FIG. 3 which depicts a simplified flow chart illustrating the functional operation of the preferred embodiment of the present invention, as embodied in the context of a device illustrated in FIG. 2. As seen, the functional operation of the present invention may be characterized into basically two parts. Generally the pre-diagnostic program samples all sensed ECGs. The pre-diagnostic program detects, in the sampled ECGs, whether normal sinus rhythm, atrial fibrillation, atrial flutter, ventricular tachycardia, ventricular flutter or ventricular fibrillation are present. If such rhythms are detected, then the device delivers the appropriate therapy. Of course, normal sinus rhythm is the most common type of rhythm of any heart. Atrial fibrillation, atrial flutter, ventricular tachycardia, ventricular flutter or ventricular fibrillation are the other more common conditions of the heart rhythm. Thus, the pre-diagnostic program is successful in achieving a diagnosis of the heart rhythm in over 95% of the time and the system of the present invention will be in a state to deliver the appropriate therapy in over 95% of the time without having to proceed through the diagnostic program. It is a further feature of the present invention that the pre-diagnostic program is designed to require a relatively low energy requirement. Thus, the pre-diagnostic program is able to operate and discriminate among the various sensed arrhythmias with a minimal battery drain. Further details regarding the operation of the pre-diagnostic program are discussed in more detail below and particularly with reference to FIG. 4.

With continued reference, however, to FIG. 3, if a normal sinus rhythm, atrial fibrillation, atrial flutter, ventricular tachycardia, ventricular flutter or ventricular fibrillation are not definitively detected by the pre-diagnostic program, then the device employs the diagnostic program. As discussed in more detail below and particularly with reference to FIGS. 6, the diagnostic program is able to discriminate among any of the possible cardiac arrhythmia's. Because, however, the pre-diagnostic program is able to render a diagnosis in over 95% of the total time, the diagnostic program will be used only very infrequently. Once the diagnostic program is employed, the device then determines whether or not a diagnosis has been reached. If a diagnosis has been successfully reached, then the device delivers the appropriate therapy. If a diagnosis has not been reached after one cycle through the diagnostic program, then the device recycles and again enters the diagnostic program with the updated sample ECG.

Figure 4:
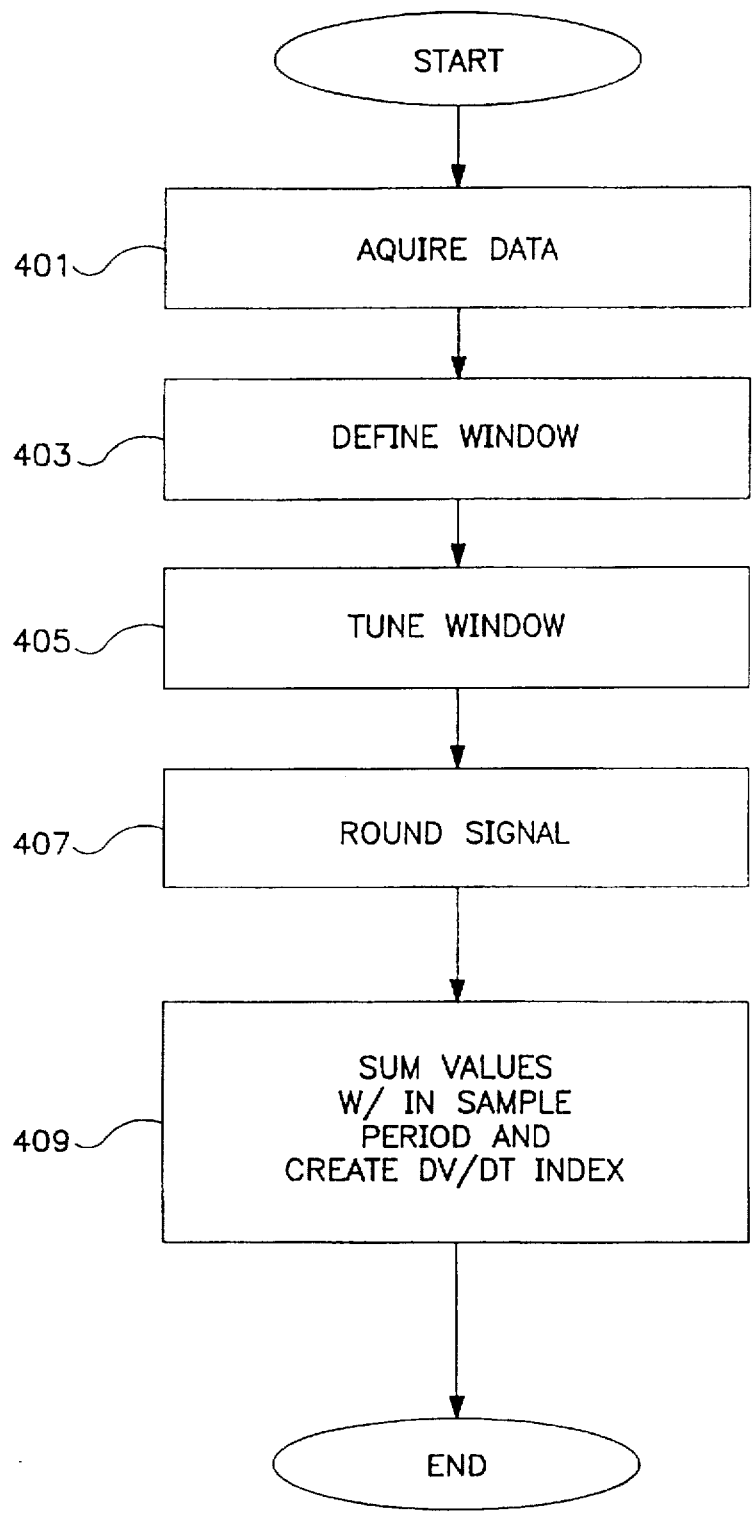
FIG. 4 is a simplified flow chart illustrating the functional operation of the pre-diagnostic program of the present invention.

Turning now to FIG. 4 which depicts the simplified flow chart illustrating the functional operation of the pre-diagnostic program of the present invention. As seen, the pre-diagnostic program operates by sampling at discrete intervals the amplitudes of the sensed ECG on an electrode. In the preferred embodiment, this sampling is performed on the high right atrial electrode. Of course, other electrodes may alternatively or concurrently be used depending upon the type of arrhythmia to be detected. If ventricular arrhythmias are to be detected, then a ventricular electrode should be used. Moreover, both an atrial electrode, such as the high right atrial electrode, as well as the ventricular electrode may be used together to detect both atrial flutter and fibrillation, as well as ventricular tachycardia, flutter and fibrillation. Sampling is preferably performed at a frequency of 250 Hz, or every 4 milliseconds for 1 second. Thus 250 samples are stored in a buffer. Next, the dv/dt is calculated from the samples stored in the buffer. Thus 125 dv/dt are calculated. These dv/dt values are then stored as absolute values in the appropriate memory location of the IPG. Once stored, a test is performed to determine if the signal that has been sensed is noise. In the preferred embodiment the testing is accomplished by determining if the maximum value is less than a constant. If it is, then noise is detected and no analysis is performed. As seen, if noise is detected, the collection is continued of the data and step one is repeated. If noise is not detected, however, then the device proceeds on to its next step. Once the noise test has been performed, the absolute maximum value for the stored dv/dt values are taken and divided by 12 and by 14. The dv/dt signals divided by 12 are shifted as a count of one while the dv/dt values divided by 14 are shifted to a count of zero. As seen, next the calculation of the mean value and the calculation of the number of values of one from the first clipped dv/dt values. Once these calculations are made, then a test is performed. In particular, the mean value is tested to determine whether it is less than 0.2, in the preferred embodiment, or whether one count value clipped are less than 25. As seen, following this operation, a true/false function is performed followed by a signal modification. Finally, total value found in the modified signal is determined.

Figure 5:
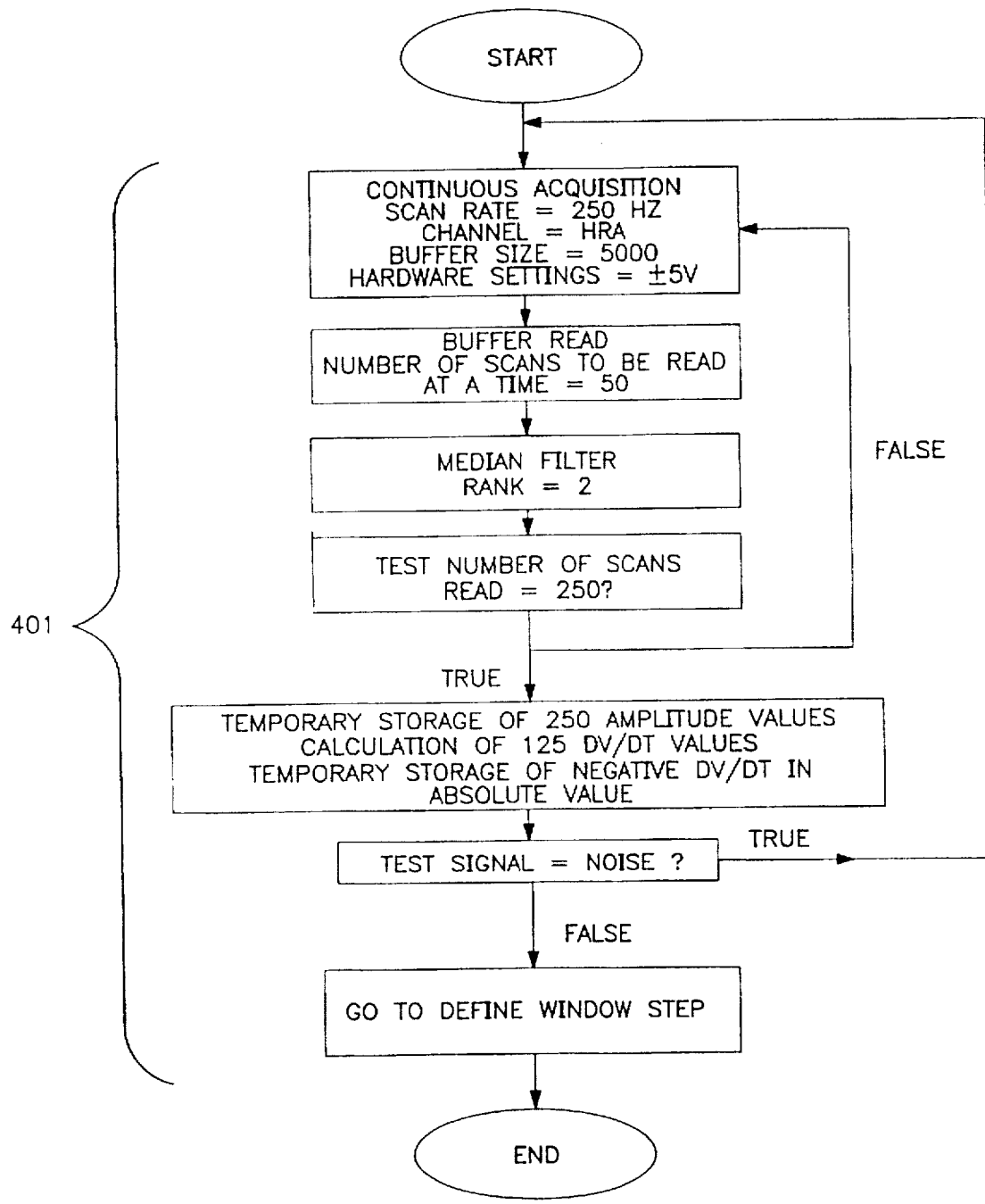
FIG. 5 is a simplified flow chart illustrating the functional operation of the acquire data step within the pre-diagnostic program shown in FIG. 4.

Turning now to FIG. 5, once the pre-diagnostic program is completed, a value is determined. As discussed above, the aim of the present algorithm and apparatus is to qualify continuously the cardiac rhythm and provide an appropriate diagnosis of any tachyarrhythmias. The present invention provides this through the provision of both the pre-diagnostic program and the diagnostic program. Essentially, the pre-diagnostic program continuously measures the voltage sensed on an electrode. In the preferred embodiment the high right atrial electrode is used, although other types of electrodes such a the ventricular or low right atrial electrode may also be used. Next the dv/dt of the sensed voltage is performed by acquiring data at discrete intervals. In the preferred embodiment every 8 milliseconds, although sampling rates may also be used. Next the data is manipulated by various processes to create an index value indicative of a particular cardiac rhythm. As discussed above, the pre-diagnostic program speeds up and automates the diagnostic processing because it provides, up to 95% of the time, a diagnosis of the current cardiac rhythm. Only during the remaining 5% or so is it required that the sensed cardiac signals be passed through the diagnostic program.

Figure 6:
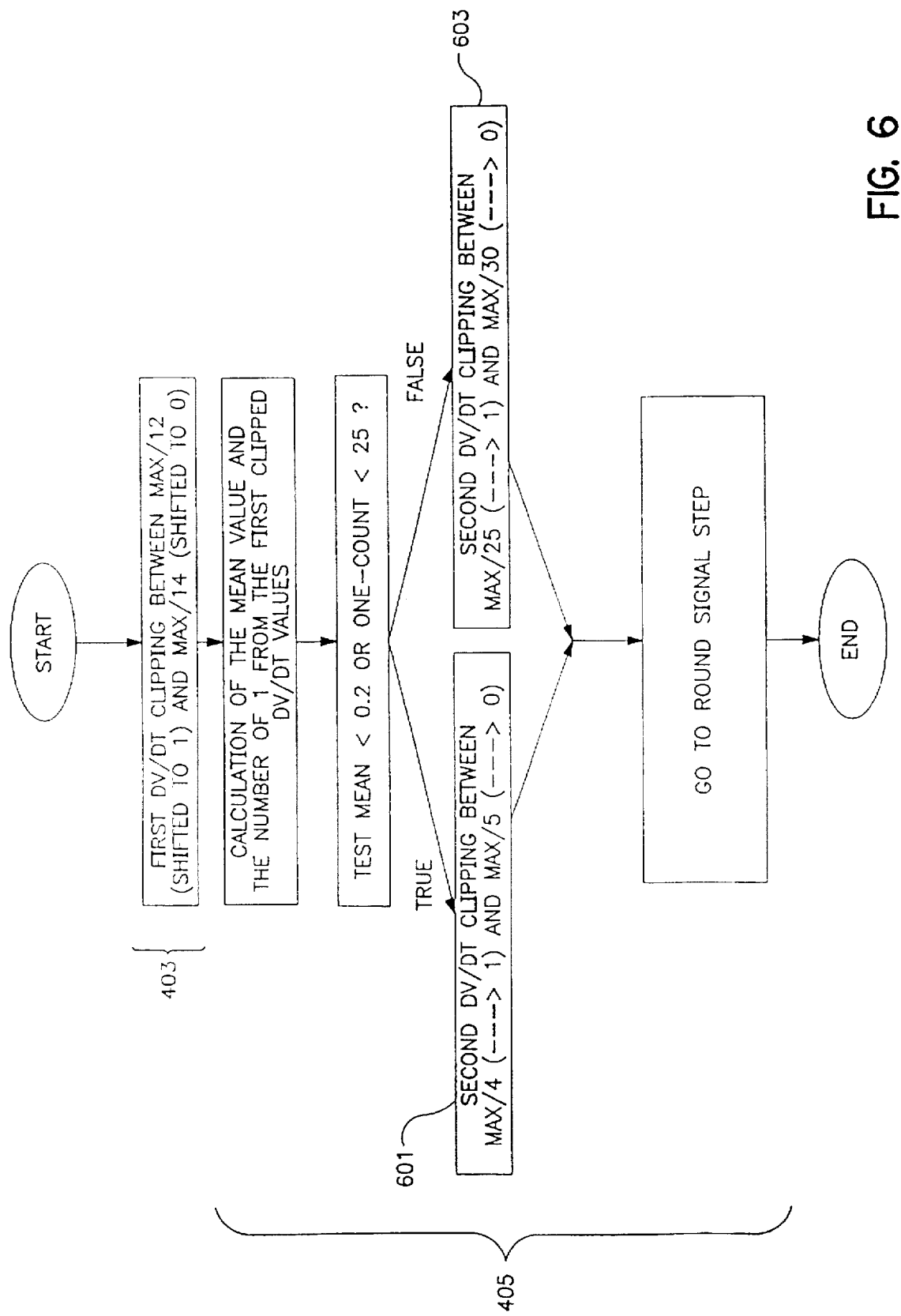
FIG. 6 is a simplified flow chart illustrating the functional operation of the define window step and tune window step within the pre-diagnostic program shown in FIG. 4.

FIG. 4 discloses the essential steps of the pre-diagnostic program. As seen, the pre-diagnostic program begins with the acquire data step 401. Further details concerning the acquisition of data during step 401 are provided in FIG. 5, discussed below. Next, a define window step 403 is carried out. The define window step 403 puts the acquired data between two fractional values of the sensed maximum dv/dt signal. An example of this is shown in FIGS. 8 and 9 discussed below. The define window step 403 is further discussed below in regards to FIG. 6. Turning again to FIG. 4, once define window step 403 is performed, the tune window step 405 is begun. Details of the tune window step 405 are shown in FIG. 6, discussed below. Once the tune window step 405 is performed, the round signal step 407 is performed, discussed in detail below with regard to FIG. 7.

Turning again to FIG. 4, once the round signal step 407 is performed the sum value step 409 is performed. The sum value step 409 creates a index value. As discussed above, this index value indicates the type of tachyarrhythmia. Particular values of the index corresponding to the appropriate diagnosis are shown in FIG. 10, discussed below.

Turning now to FIG. 5, this details the acquire data step 401. As seen, the acquire data step 401 begins by continuously acquiring data at a scan rate, in the preferred embodiment, 250 Hz. Once the scan is performed, the data is read into a buffer, filtered and, if the number of acquired scans is equal to 250, then these values are temporarily stored so that the calculation of the dv/dt values of 125 data points may be acquired. Next, the 125 dv/dt values are tested to determine if they are representative of noise. Any type of suitable test for noise may be used. In the preferred embodiment the test used consists of determining whether the maximum dv/dt is less than a preset amount or maximum amplitude of the sensed ECG is less than a second preset amount, then the acquire data step 401 resets itself and begins again acquiring data. If not, however, then the acquire data step 401 is completed and the define window step 403 is begun. The define window step 403 and tune window step 405 are shown in FIG. 6.

As seen in FIG. 6, the define window step 403 essentially comprises clipping and resealing the signals between two fractions of the maximum dv/dt value sensed. In the preferred embodiment, the clipping is performed between the dv/dt max over 12 (which shifts the values to 1) and the dv/dt max/14 (shifted to the 0 value). Once such a window is defined, it is then tuned to the precise parameters required. The tune window step 405 essentially has three substeps. In the first substep the calculation of the mean value and the number of one from the first clipped dv/dt value is performed. Once this is performed, then a test is performed. In particular, if the mean is less than 0.2 or one count is less than 25, then either normal sinus rhythm or flutter is indicated and a second clipping step 601 is performed. As seen, step 601 provides a second dv/dt clipping between the maximum dv/dt divided by 4 (which is shifted to 1) and the maximum dv/dt divided by 5 (which is shifted to 0). If, however, the test mean is greater than 0.2 or one count is greater than 25, then a fibrillation is indicated and another type of clipping step is performed. As seen, second clipping step 603 provides a second dv/dt clipping between the maximum dv/dt divided by 25 (which is shifted to 1) and the maximum dv/dt divided by 30 (which is shifted to 0).

Through these second clipping steps, depending upon whether the test count indicate a normal sinus rhythm or flutter or fibrillation, the window of analysis is tuned to the appropriate rhythm and adapted to the particular type of rhythm sensed. Once such window tuning is performed, the device proceeds to the next step, round signal step 407, best seen in FIG. 7.

Figure 7:
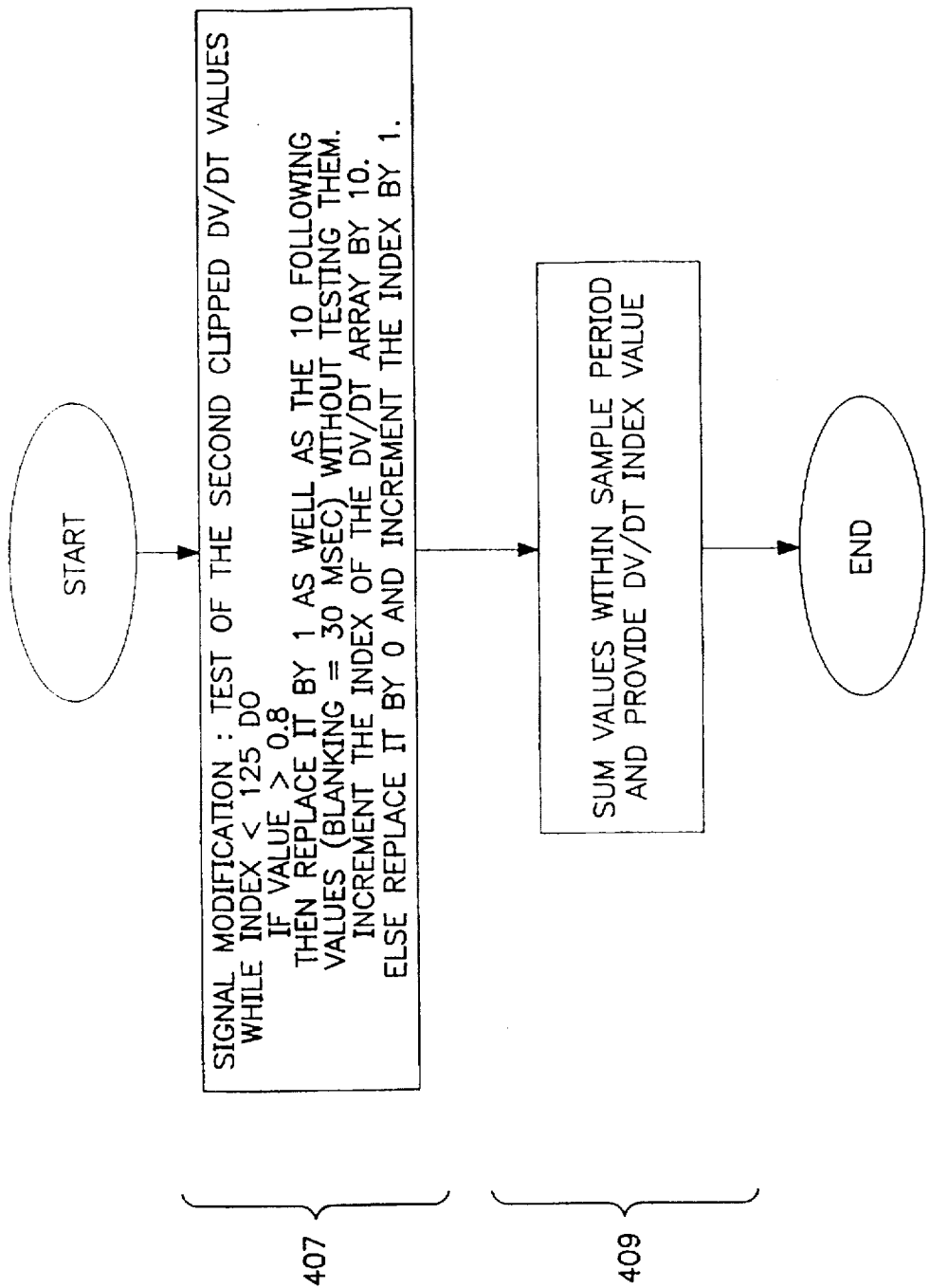
FIG. 7 is a simplified flow chart illustrating the functional operation of the round signal step within the pre-diagnostic program shown in FIG. 4.

Turning now to FIG. 7, is seen the round signal step rounds up any values of the defined window which are greater than 0.8 to the value of 1. The following 10 values are also defined as equaling 1 and the dv/dt counter is indexed by 10. If the value is less than 0.1, then it is rounded down to the value of 0 and the index is only incremented by the value 1.

Once the round signal step 407 is performed, then the sum value step 409 is performed. In particular, the sum value step 409 takes the values within the sample period and sums them and provides from the summation a dv/dt index value. Once the sum value step 409 is performed, then the dv/dt index value is used to determine whether an arrhythmia is present. In particular, turning again to FIG. 3, if either normal sinus rhythm, atrial flutter or fibrillation or ventricular tachycardia, flutter or fibrillation is present, then an appropriate therapy is delivered. In addition, in the preferred embodiment the detected arrhythmia is stored in RAM memory for future downloading. Otherwise, then the diagnostic program is utilized.

Two examples of the operation of the pre-diagnostic program may be seen in FIGS. 8 and 9. As seen in FIG. 8, the high right atrial signals are sensed, in particular, the voltage over the time. Next, the dv/dt of the same period of sensed high right atrial signals are determined. If the sensed signals are not found to be noise, then the acquired data step is completed and the defined window and tune window steps are begun. As seen in FIG. 8, the signal is first subjected to a clipping such that the dv/dt max divided by 12 is shifted as 1 and the dv/dt max divided by 14 is shifted to 0. Once so performed, several other calculations as discussed in regard to FIG. 6 are performed and then a second dv/dt clipping is performed. Once such a second such dv/dt clipping is performed, then a round signal step is performed and a summation value step is performed such that a dv/dt index is created. As seen in FIG. 8, the dv/dt index created is equal to 4 based on the second dv/dt clipping. As detailed in FIG. 10, such a dv/dt index indicates the sensed high right atrial signal had a tachyarrhythmia which was atrial flutter.

FIG. 9 illustrates a second sensed high right atrial signal and the following steps used to determine the type of tachyarrhythmia sensed. As seen, the second dv/dt clipping of FIG. 9 has many more high points than that of FIG.8. In particular, the dv/dt index is sensed as being 11. As seen in FIG. 10, this value 11 indicates atrial fibrillation is occurring.

As discussed above, FIG. 10 illustrates the values of the dv/dt index which indicate a particular type of tachyarrhythmia. As seen, the values depend upon whether the sensed signal analyzed is either from the high right atrial electrode or the ventricular electrode. If the high right atrial electrode is used, then the dv/dt index values which indicate a tachyarrhythmia are one set of values, whereas if the ventricular channel is used, a different set of values are used.

Although in the preferred embodiment only a single electrode is used during the pre-diagnostic program, it is contemplated both electrodes could be used and the two electrodes and determined index values may be used to provide a more refined diagnosis. In fact, the two electrodes could be used independently of one another such that only an atrial tachyarrhythmia would be diagnosed using the high right atrial electrode while a ventricular arrhythmia would be diagnosed using only the ventricular electrode.

Figure 11:
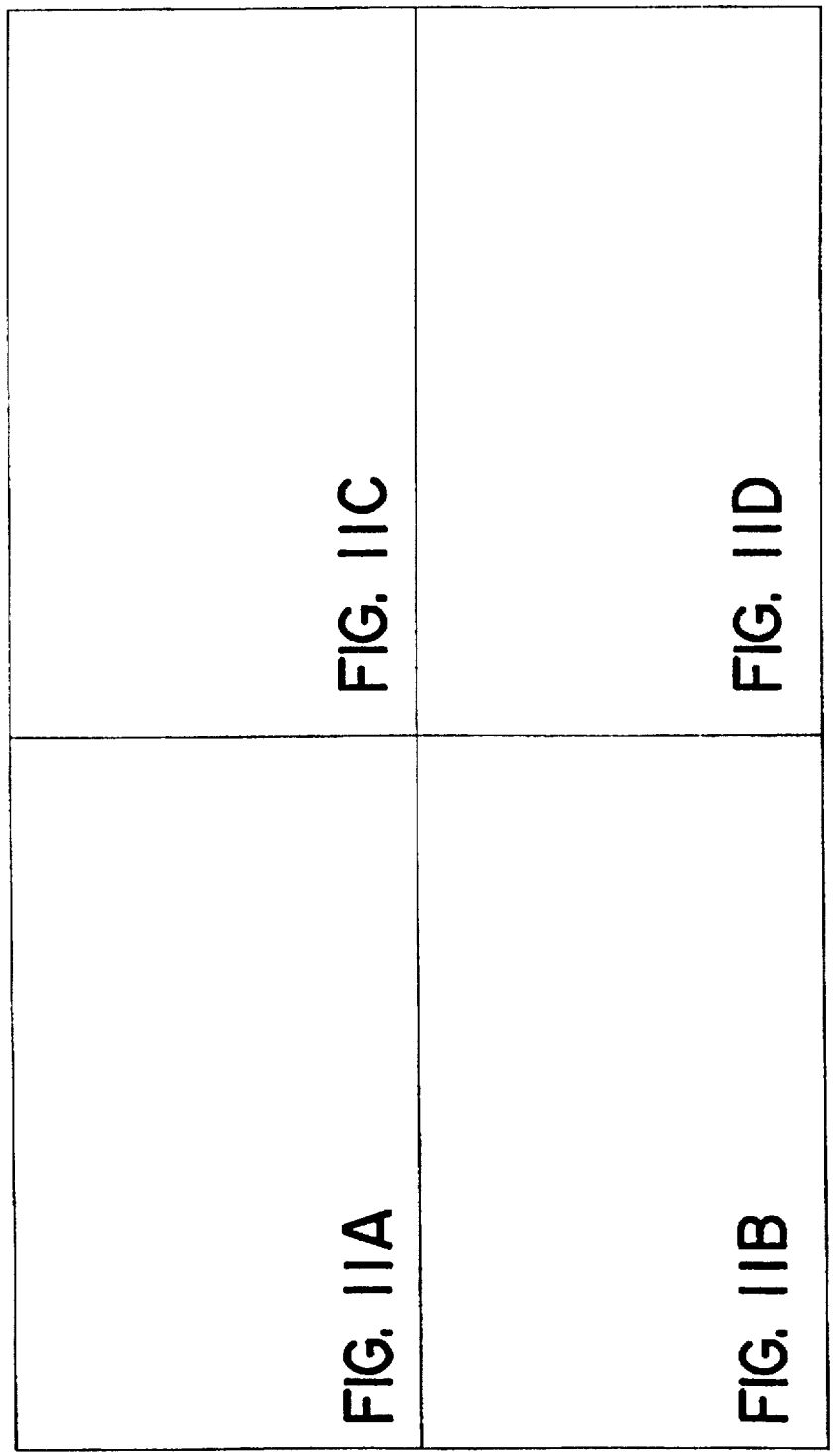

As discussed above, FIG. 11 is a depiction of the values used in the diagnostic program. Essentially, the diagnostic program comprises a matrix of sensed ECG values plotted against the indicated diagnosis. As discussed above, 13 parameters of the ECG are examined. By examining each of the 13 parameters, a specific diagnosis may be reached. The 13 parameters sensed are as follows: direction, propagation (or conduction time), analysis of intervals (PR vs. RP), ventricular rate vs. programmed upper rate limit, atrial rate vs. programmed upper rate limit, ventricular rate vs. programmed lower rate, atrial rate vs. programmed lower rate, P count versus R count, ventricular rhythm, atrial rhythm, tachycardia onset, site of prematurity, AV conduction. As seen in this FIG. 11, 55 separate diagnoses of arrhythmias may be reached. Thus, using the diagnostic program, any arrhythmias not able to be diagnosed using the pre-diagnostic program may be diagnosed using the diagnostic program. Once the diagnostic program is completed and a diagnosis has been reached, then the delivery of therapy is initiated and the detected arrhythmia is stored in RAM memory for future downloading. If a diagnosis is not reached, then the diagnostic program is reentered on the following QRS complex.

Although a specific embodiment of the invention has been disclosed, this is done for purposes of illustration and is not intended to be limiting with regard to the scope of the invention. It is contemplated various substitutions, alterations and/or modifications may be made to the disclosed embodiment without departing from the spirit and scope of the invention. Such modifications may include substituting elements or components which perform substantially the same function in substantially the same way to achieve substantially the same result for those described herein. For example, it is contemplated the PDP and DP may be usefully employed also in the context of a passive implantable monitor, such as a Holter monitor. In this fashion, the present invention may be used to continuously monitor and provide a diagnosis of sensed cardiac events. Such as system may be implemented using any electrode configuration, such as whole ring bipoles, as well as tripoles or even quadrapoles. Such as system may also be implemented to use on or more of the electrodes to sense, such as the atrial or ventricular electrodes, for example.

What is claimed is:

1. An implantable system for providing electrical stimulation to a body organ comprising:

means for sensing signals in a first chamber of a patient's heart;

a first detection apparatus requiring a first level of power, the first detection apparatus having means for acquiring discrete values of the sensed signals in the first chamber of the patient's heart, the means for acquiring discrete values of the sensed signal having a means for detecting noise, means for defining a first window within which the acquired values are clipped and positioned, means for measuring the clipped and positioned values, the means for measuring indicating either a first parameter or a second parameter, means for defining a second window within which the first window values are further clipped and positioned if a first parameter is indicated; means for defining a third window within which the first window values are further clipped and positioned if a second parameter is indicated; means for rounding either the second window or the third window value range, means for summing the rounded second window values or the third window values to create an index value;

means for storing a pre-defined range of index values;

means for comparing the created index value to the stored range of index values, the means for comparing creating a therapy delivery instruction or a further detect instruction; and means for generating electrical stimulus signals for delivery to a second chamber of a patient's heart according to a programmed protocol;

a second detection apparatus requiring a second level of power, the second level of power being greater than the first level of power, the second detection apparatus responding to the further detect instruction, the second detection apparatus comprising means for storing a plurality of different predetermined patterns, each respective pattern containing a set of predetermined parameters representative of a respective cardiac rhythm, means for comparing the sensed signals with the stored plurality of different predetermined patterns, and means for indicating a diagnosed rhythm on the basis of the means for comparing;

means for generating electrical stimulus signals for delivery to the second chamber of a patient's heart in response to the therapy delivery instruction or the further detect instruction.

2. The implantable system of claim 1 wherein the means for sensing signals in the patient's first chamber of the heart comprises a medical electrical lead having a first electrode positioned in a first chamber of the patient's heart and a second electrode positioned in a first chamber of the patient's heart.

3. The implantable system of claim 2 wherein the first electrode comprises a whole ring bi-pole electrode.

4. The implantable system of claim 1 further comprising a hermetic enclosure enclosing the first detection apparatus, the means for storing a pre-defined range of index values, the means for comparing the created index value to the stored range of index values, the second detection apparatus, and the means for generating electrical stimulus signals for delivery to the second chamber of a patient's heart.

5. The implantable system of claim 1 wherein the means for sensing signals in a first chamber of the patient's heart comprises a means for sensing signals in the right atrium.

6. The implantable system of claim 1 wherein the means for sensing signals in a first chamber of the patient's heart comprises a means for sensing signals in the right ventricle.

7. The implantable system of claim 1 wherein the means for generating electrical stimulus in a second chamber of the patient's heart comprises a means for stimulating the right ventricle.

8. The implantable system of claim 1 wherein the means for sensing signals in the patient's first chamber of the heart comprises a medical electrical lead having a first electrode positioned in an upper area within a first chamber of the patient's heart and a second electrode positioned within a lower area within a first chamber of the patient's heart.

9. The implantable system of claim 1 wherein the means for storing a plurality of different predetermined patterns, each respective pattern containing a set of predetermined parameters representative of a respective cardiac rhythm, comprises means for storing direction, propagation (or conduction time), analysis of intervals (PR vs. RP), ventricular rate vs. programmed upper rate limit, atrial rate vs. programmed upper rate limit, ventricular rate vs. programmed lower rate, atrial rate vs. programmed lower rate, P count versus R count, ventricular rhythm, atrial rhythm, tachycardia onset, site of prematurity, AV conduction of a sensed signal in the patient's first chamber of the heart.

10. An implantable system for providing electrical stimulation to a body organ comprising:

means for sensing signals in a first chamber of a patient's heart;

a first detection apparatus, the first detection apparatus having means for acquiring discrete values of the sensed signals in the first chamber of the patient's heart, the means for acquiring discrete values of the sensed signal having a means for detecting noise, means for defining a first window within which the acquired values are clipped and positioned, means for measuring the clipped and positioned values, the means for measuring indicating either a first parameter or a second parameter, means for defining a second window within which the first window values are further clipped and positioned if a first parameter is indicated; means for defining a third window within which the first window values are further clipped and positioned if a second parameter is indicated; means for rounding either the second window or the third window value range, means for summing the rounded second window values or the third window values to create an index value;

means for storing a pre-defined range of index values;

means for comparing the created index value to the stored range of index values, the means for comparing creating a therapy delivery instruction or a further detect instruction; and means for generating electrical stimulus signals for delivery to a second chamber of a patient's heart according to a programmed protocol;

a second detection apparatus, the second detection apparatus responding to the further detect instruction, the second detection apparatus comprising means for storing a plurality of different predetermined patterns, each respective pattern containing a set of predetermined parameters representative of a respective cardiac rhythm, means for comparing the sensed signals with the stored plurality of different predetermined patterns, and means for indicating a diagnosed rhythm on the basis of the means for comparing;

means for generating electrical stimulus signals for delivery to the second chamber of a patient's heart in response to the therapy delivery instruction or the further detect instruction.

11. The implantable system of claim 10 wherein the first detection apparatus uses a first level of power and the second detection apparatus uses a second level of power, the first level less than the second level.

12. The implantable system of claim 10 wherein the means for sensing signals in the patient's first chamber of the heart comprises a medical electrical lead having a first electrode positioned in a first chamber of the patient's heart and a second electrode positioned in a first chamber of the patient's heart.

13. The implantable system of claim 12 wherein the first electrode comprises a whole ring bi-pole electrode.

14. The implantable system of claim 10 further comprising a hermetic enclosure enclosing the first detection apparatus, the means for storing a pre-defined range of index values, the means for comparing the created index value to the stored range of index values, the second detection apparatus, and the means for generating electrical stimulus signals for delivery to the second chamber of a patient's heart.

15. The implantable system of claim 10 wherein the means for sensing signals in a first chamber of the patient's heart comprises a means for sensing signals in the right atrium.

16. The implantable system of claim 10 wherein the means for sensing signals in a first chamber of the patient's heart comprises a means for sensing signals in the right ventricle.

17. The implantable system of claim 10 wherein the means for generating electrical stimulus in a second chamber of the patient's heart comprises a means for stimulating the right ventricle.

18. The implantable system of claim 10 wherein the means for sensing signals in the patient's first chamber of the heart comprises a medical electrical lead having a first electrode positioned in an upper area within a first chamber of the patient's heart and a second electrode positioned within a lower area within a first chamber of the patient's heart.

19. The implantable system of claim 10 wherein the means for storing a plurality of different predetermined patterns, each respective pattern containing a set of predetermined parameters representative of a respective cardiac rhythm, comprises means for storing direction, propagation (or conduction time), analysis of intervals (PR vs. RP), ventricular rate vs. programmed upper rate limit, atrial rate vs. programmed upper rate limit, ventricular rate vs. programmed lower rate, atrial rate vs. programmed lower rate, P count versus R count, ventricular rhythm, atrial rhythm, tachycardia onset, site of prematurity, AV conduction of a sensed signal in the patient's first chamber of the heart.

* * * * *